United States Patent
Romanowski et al.

(10) Patent No.: US 10,295,815 B2
(45) Date of Patent: May 21, 2019

(54) AUGMENTED STEREOSCOPIC MICROSCOPY

(71) Applicant: Arizona Board of Regents on Behalf of the University of Arizona, Tucson, AZ (US)

(72) Inventors: Marek Romanowski, Tucson, AZ (US); Jeffrey Watson, Tucson, AZ (US); Christian Gainer, Berkeley, CA (US)

(73) Assignee: Arizona Board of Regents on Behalf of the University of Arizona, Tucson, AZ (US)

( * ) Notice: Subject to any disclaimer, the term of this patent is extended or adjusted under 35 U.S.C. 154(b) by 0 days.

(21) Appl. No.: 15/548,807

(22) PCT Filed: Feb. 5, 2016

(86) PCT No.: PCT/US2016/016747
§ 371 (c)(1),
(2) Date: Aug. 4, 2017

(87) PCT Pub. No.: WO2016/130424
PCT Pub. Date: Aug. 18, 2016

(65) Prior Publication Data
US 2018/0024341 A1    Jan. 25, 2018

Related U.S. Application Data

(60) Provisional application No. 62/113,784, filed on Feb. 9, 2015.

(51) Int. Cl.
*G02B 21/22* (2006.01)
*G02B 21/16* (2006.01)
(Continued)

(52) U.S. Cl.
CPC ......... *G02B 21/22* (2013.01); *G02B 21/0012* (2013.01); *G02B 21/02* (2013.01);
(Continued)

(58) Field of Classification Search
CPC ...... G02B 21/22; G02B 21/02; G02B 21/365; G02B 21/06; G02B 21/361; G02B 21/16;
(Continued)

(56) References Cited

U.S. PATENT DOCUMENTS 8,144,399 B2   3/2012   Steenblik et al.
8,482,859 B2   7/2013   Border et al.
(Continued)

FOREIGN PATENT DOCUMENTS

EP   2199842 A1   6/2010
WO   01/74264 A1   10/2001
(Continued)

OTHER PUBLICATIONS

International Search Report for PCT/US2016/016747 dated Apr. 14, 2016.
(Continued)

*Primary Examiner* — Frank G Font
(74) *Attorney, Agent, or Firm* — Thomas Horstemeyer, LLP

(57) ABSTRACT

Various examples are provided related to imaging with augmented stereoscopic microscopes. In one example, an augmented stereoscopic microscope includes an objective lens that can simultaneously receive near infrared (NIR) images and visible bright-field images of an examined object and an augmentation module. The augmentation module can separate the NIR images from the visible bright-field images for processing by an image processing unit to produce synthetic images using the NIR images and combine the synthetic images with the visible bright-field images to form
(Continued)

co-registered augmented images that are directed to an eyepiece of the augmented stereoscopic microscope. In another example, a method includes obtaining a NIR image of an examined object; generating a synthetic image using the NIR image; combining the synthetic image with a real-time visual image of the examined object to form an augmented image; and directing the augmented image to an eyepiece of an augmented stereoscopic microscope.

23 Claims, 12 Drawing Sheets

(51) Int. Cl.
    *G02B 21/06*     (2006.01)
    *G02B 21/02*     (2006.01)
    *G02B 21/36*     (2006.01)
    *G02B 21/00*     (2006.01)
    *A61B 1/00*     (2006.01)
    *A61B 1/313*     (2006.01)

(52) U.S. Cl.
    CPC ............ *G02B 21/06* (2013.01); *G02B 21/16* (2013.01); *G02B 21/361* (2013.01); *G02B 21/365* (2013.01); *A61B 1/0005* (2013.01); *A61B 1/00009* (2013.01); *A61B 1/3132* (2013.01)

(58) Field of Classification Search
    CPC .. A61B 1/04; A61B 1/05; A61B 19/00; A61B 34/30; A61B 90/30; A61B 2090/364; H04N 13/00
    USPC ....... 359/385, 388; 348/45; 600/111; 901/15
    See application file for complete search history.

(56) References Cited

U.S. PATENT DOCUMENTS

| | | | |
|---|---|---|---|
| 8,614,851 B2 | 12/2013 | Kuster | |
| 2004/0070822 A1 | 4/2004 | Shioda et al. | |
| 2006/0175550 A1* | 8/2006 | Siddiqi | G02B 21/16 250/338.1 |
| 2009/0268010 A1 | 10/2009 | Zhao et al. | |
| 2010/0056928 A1* | 3/2010 | Zuzak | A61B 5/0071 600/476 |
| 2010/0110538 A1* | 5/2010 | Steffen | G02B 21/16 359/363 |
| 2011/0275932 A1* | 11/2011 | Leblond | A61B 5/0062 600/425 |
| 2013/0253312 A1 | 9/2013 | Sato et al. | |
| 2015/0198797 A1* | 7/2015 | Andre | A61B 5/7425 348/80 |
| 2018/0303667 A1* | 10/2018 | Peyman | A61F 9/00821 |

FOREIGN PATENT DOCUMENTS

| | | |
|---|---|---|
| WO | 2008/154043 A1 | 12/2008 |
| WO | 2009/131840 A1 | 10/2009 |

OTHER PUBLICATIONS

Edwards, et al, "Augmentation of Reality Using an Operating Microscope for Otolaryngology and Neurosurgical Guidance", Journal of Image Guided Surgery, 1:172-178 (1995).

"An Operational Near-Infrared Fluorescence Imaging System Prototype for Large Animal Surgery" by A.M. De Grand et al., Technology in Cancer Research & Treatment, vol. 2, No. 6, Dec. 2003.

"Gold Nanorods Targeted to Delta Opioid Receptor: Plasmon-Resonant Contrast and Photothermal Agents" by K.C. Black et al., Molecular Imaging, vol. 7, No. 1 Feb. 2008, pp. 50-57.

"Light-Activated Content Release from Liposomes" by S.J. Leung et al., Theranostics 2(10):1020-1036, Oct. 2012.

"Augmented microscopy with near-infrared fluorescence detection" by J.R. Watson et al., Proc. SPIE 9311, Molecular-Guided Surgery: Molecules, Devices, and Applications, 93110I (Mar. 2015).

"Integration of ICG videoangiography with operative microscope: Augmented reality for interactive assessment of vascular structures and blood flow" by N.L. Martyrosyan et al., Neurosurgery. Jun. 2015; 11(Suppl 2): 252-258.

"Augmented Microscopy—Simultaneous Acquisition of Bright Field and Luminescence Lifetime Images" by C. Gainer et al. American Society for Laser in Surgery and Medicine, 30th Annual Conference 2010 (Abstract only).

"Fluorescence-Guided Tumor Visualization Using the Tumor Paint BLZ-100" by D.S. Kittle et al., Cureus 6(9): e210; Sep. 2014.

Vahrmeijer, A. L., Hutteman, M., Van Der Vorst, J. R., Van De Velde, C. J. H., Vahrmeijer, A. L., Hutteman, M., Frangioni, J. V. (Sep. 2013). Image-guided cancer surgery using near-infrared fluorescence. Nature Publishing Group, 10(10). https://doi.org/10.1038/nrclinonc.2013.123.

Kersten-Oertel, M., Gerard, I., Drouin, S., Mok, K., Sirhan, D., Sinclair, D. S., & Collins, D. L. (Feb. 2015). Augmented reality in neurovascular surgery: feasibility and first uses in the operating room. International Journal of Computer Assisted Radiology and Surgery, 10(11), 1823-1836. https://doi.org/10.1007/s11548-015-1163-8.

Chi, C., Du, Y., Ye, J., Kou, D., Qiu, J., Wang, J., Chen, X. (Aug. 2014). Intraoperative Imaging-Guided Cancer Surgery: From Current Fluorescence Molecular Imaging Methods to Future Multi-Modality Imaging Technology. Theranostics, 4(411), 1072-1084. https://doi.org/10.7150/thno.9899.

Mondal, S. B., Gao, S., Zhu, N., Sudlow, G. P., Liang, K., Som, A., Achilefu, S. (Jul. 2015). Binocular Goggle Augmented Imaging and Navigation System provides real-time fluorescence image guidance for tumor resection and sentinel lymph node mapping. Scientific Reports, 5(Jul.), 12117. https://doi.org/10.1038/srep12117.

Liu, Y., Bauer, A. Q., Akers, W. J., Sudlow, G., Liang, K., Shen, D., Louis, S. (May 2011). Hands-free, wireless goggle for near-infrared fluorescence and real-time image-guided surgery From the Departments of Radiology a and Biomedical Engineering. Surgery, 149, 689-698. https://doi.org/10.1016/j.surg.2011.02.007.

Sarder, P., Gullicksrud, K., Mondal, S., Sudlow, G. P., Achilefu, S., & Akers, W. J. (Dec. 2013). Dynamic optical projection of acquired luminescence for aiding oncologic surgery. Journal of biomedical optics, 18(12), 120501-120501.

Elliott, J. T., Dsouza, A. V., Marra, K., Pogue, B. W., Roberts, D. W., & Paulsen, K. D. (Sep. 2016). Microdose fluorescence imaging of ABY-029 on an operating microscope adapted by custom illumination and imaging modules. Biomedical Optics Express, 7(9), 3280. https://doi.org/10.1364/BOE.7.003280.

* cited by examiner

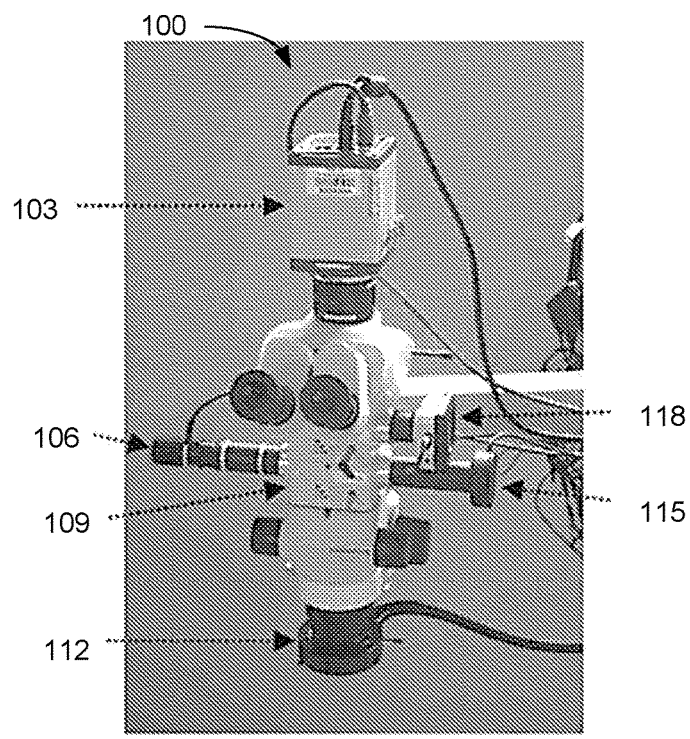
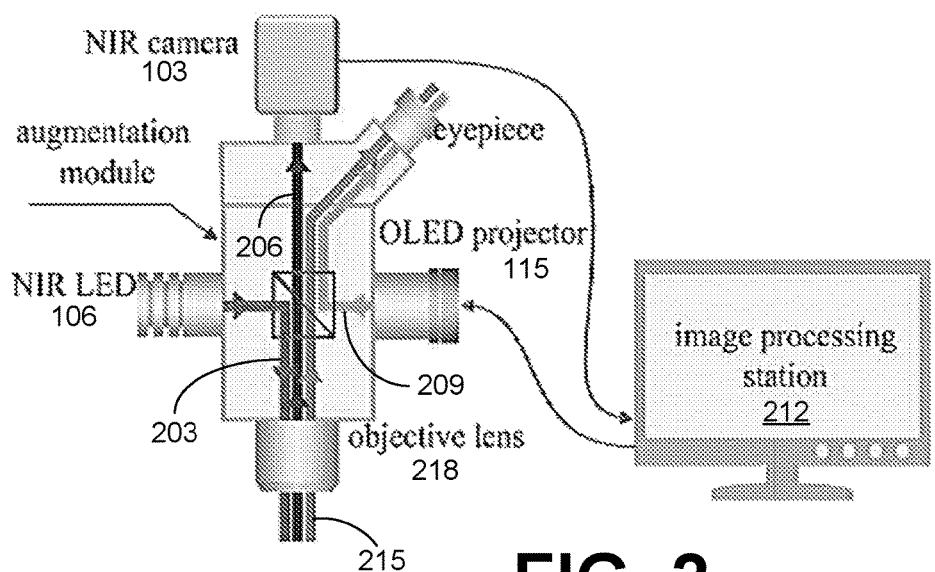
FIG. 1B
FIG. 2

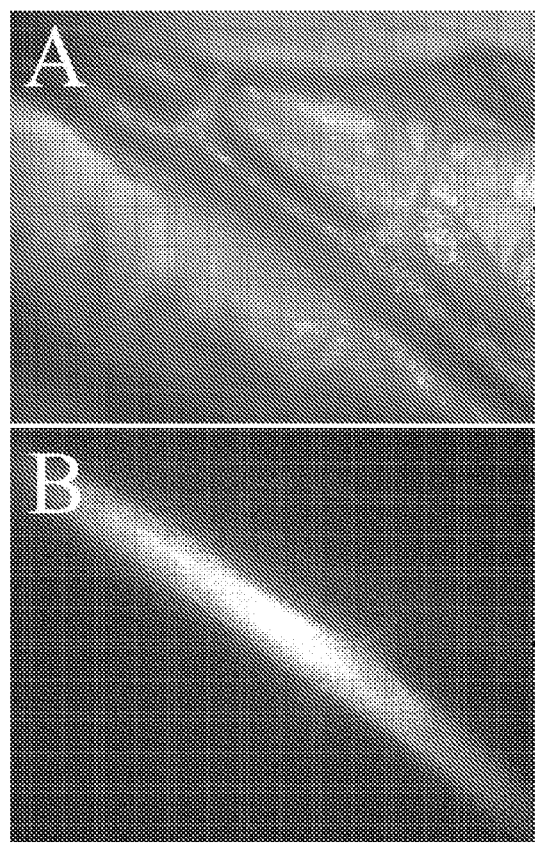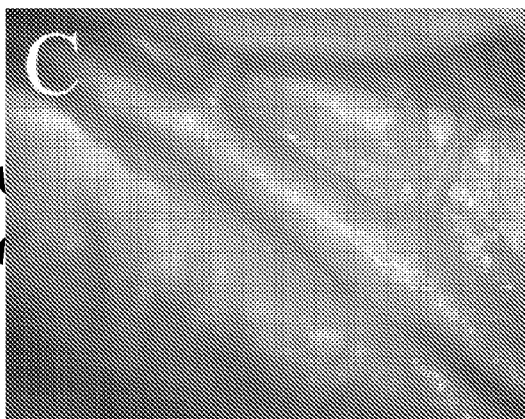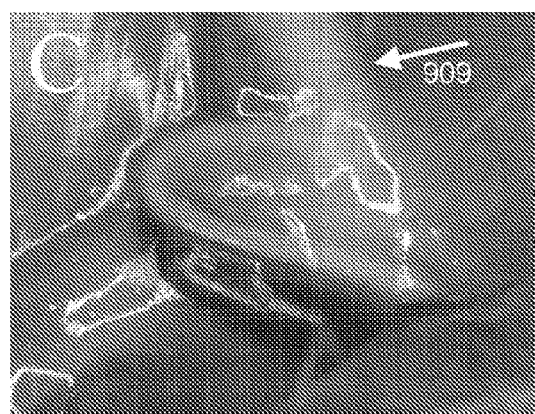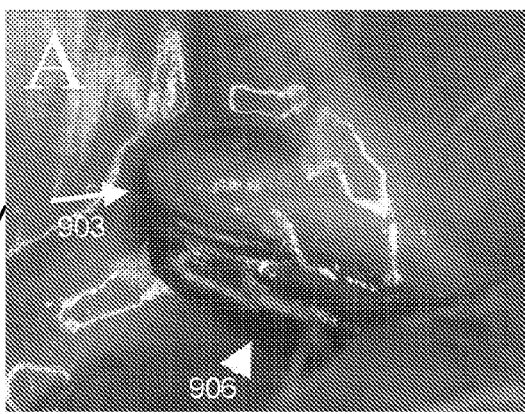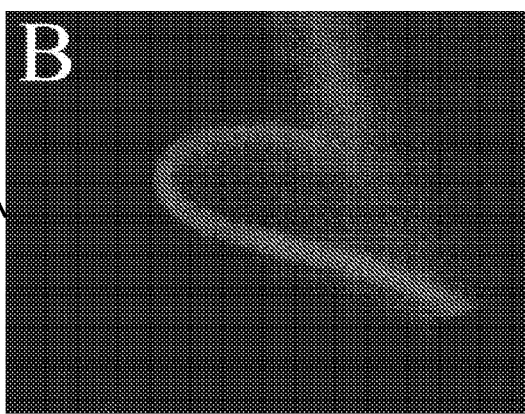
FIG. 8
FIG. 9

FIG. 14C  FIG. 14D

AUGMENTED STEREOSCOPIC MICROSCOPY

CROSS REFERENCE TO RELATED APPLICATIONS

This application is the 35 U.S.C. § 371 national stage application of PCT Application No. PCT/US2016/016747, filed Feb. 5, 2016, where the PCT claims priority to, and the benefit of, U.S. provisional application entitled "Augmented Stereoscopic Surgical Microscope" having Ser. No. 62/113,784, filed Feb. 9, 2015, both of which are herein incorporated by reference in their entireties.

STATEMENT REGARDING FEDERALLY SPONSORED RESEARCH OR DEVELOPMENT

This invention was made with government support under Grant Nos. CA120350 and T32 HL007955, awarded by NIH. The Government has certain rights in the invention.

BACKGROUND

Stereoscopic microscopes are used to produce a three-dimensional visualization of a sample or physical feature being examined. The instrument uses two separate optical paths with two objectives and eyepieces to provide slightly different viewing angles to the left and right eyes. The stereo microscope is often used to study or to carry out close work such as dissection, microsurgery, art restoration, and/or device and circuit board manufacture or inspection. One of the limitations to current surgical cancer treatment is boundary delineation, and accurately identifying tumor margins remains of paramount importance during surgical resection of cancerous tissue.

SUMMARY

Embodiments of the present disclosure are related to imaging with augmented stereoscopic microscopes. In one embodiment, among others, an augmented stereoscopic microscope comprises an objective lens configured to simultaneously receive near infrared (NIR) images and visible bright-field images of an examined object and an augmentation module. The augmentation module can be configured to separate the NIR images from the visible bright-field images for processing by an image processing unit to produce synthetic images based upon the NIR images and combine the synthetic images with the visible bright-field images to form co-registered augmented images that are directed to an eyepiece of the augmented stereoscopic microscope. In some embodiments, the augmentation module can be configured to merge the visible bright-field image with a synthetic image obtained from an image processing unit. The synthetic image can be based upon the NIR images received by the microscope or other types of captured images. In one or more aspects of these embodiments, the augmentation module can comprise a beamsplitter configured to combine the synthetic images with the visible bright-field images to form the co-registered augmented images. Combining the synthetic images with the visible bright-field images can comprise projecting the synthetic images onto the beamsplitter to overlay the visible bright-field images. The beamsplitter can be a dichroic beamsplitter.

In one or more aspects of these embodiments, the augmentation module can comprise a spatial light modulator configured to combine the synthetic images with the visible bright-field images to form the co-registered augmented images. The spatial light modulator can be a switchable mirror such as a micromirror array. Combining the synthetic images with the visible bright-field images can comprise switching at least a portion of the micromirror array to reflect at least a portion of the synthetic images and at least a portion of the visible bright-field images. The synthetic images can comprise visible pseudo-color images. The augmentation module can comprise a light emitting diode (LED) configured to illuminate the object with NIR excitation light via the objective lens. The augmentation module can comprise a sensor configured to capture the NIR images. The sensor can be configured to capture the co-registered augmented images. The augmentation module can comprise a sensor configured to capture the co-registered augmented images.

In one or more aspects of these embodiments, the augmentation module can comprise a short-pass filter configured to remove NIR light from the co-registered augmented images. The augmentation module can be configured to form co-registered augmented images for a right optical path of the augmented stereoscopic microscope and co-registered augmented images for a left optical path of the augmented stereoscopic microscope. The synthetic images can comprise prerecorded information associated with the examined object. The prerecorded information can be obtained through magnetic resonance imaging (MRI), computed tomography (CT), or positron emission tomography (PET) of the examined object. The synthetic image can comprise a chemical concentration in the examined object. The synthetic image can comprise a temperature of the examined object.

In another embodiment, among others, a method comprises generating a synthetic image; combining the synthetic image with a real-time visual image of the examined object to form an augmented image; and directing the augmented image to an eyepiece of an augmented stereoscopic microscope. The synthetic image can be based upon a near infrared (NIR) image obtained of an examined object. In one or more aspects of these embodiments, combining the synthetic image with the real-time visual image can comprise projecting the synthetic image onto a beamsplitter to overlay the real-time visual image. Combining the synthetic image with the real-time visual image can comprise switching at least a portion of a micromirror array to reflect at least a portion of the synthetic image and at least a portion of the real-time visual image.

In one or more aspects of these embodiments, the method can comprise Illuminating the examined object with NIR excitation through an objective lens of the augmented stereoscopic microscope. The examined object can comprise a NIR laser. The synthetic image can comprise prerecorded information associated with the examined object. The prerecorded information can be obtained through magnetic resonance imaging (MRI), computed tomography (CT), or positron emission tomography (PET) of the examined object. The synthetic image can comprise a chemical concentration in the examined object. The synthetic image can comprise a temperature of the examined object.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims. In addition, all optional and preferred features and modifications of the described embodiments are usable in all aspects of the disclosure taught herein. Furthermore, the individual features of the dependent claims, as well as all optional and preferred features and modifications of the described embodiments are combinable and interchangeable with one another.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

Referring to FIGS. 1A and 1B, shown is an example of an augmented stereoscopic microscope 100 in accordance with various embodiments of the present disclosure.

FIGS. 2, 3, 4A and 4C are schematic representations of various examples of the augmented microscope of FIGS. 1A and 1B in accordance with various embodiments of the present disclosure.

FIGS. 7 through 9 are images illustrating augmentation of visual images using the augmented microscope of FIGS. 1A and 1B in accordance with various embodiments of the present disclosure.

FIGS. 14B through 14E illustrate the operation of a micromirror array of the augmented microscope of FIG. 14A in accordance with various embodiments of the present disclosure.

DETAILED DESCRIPTION

Figure 1A:
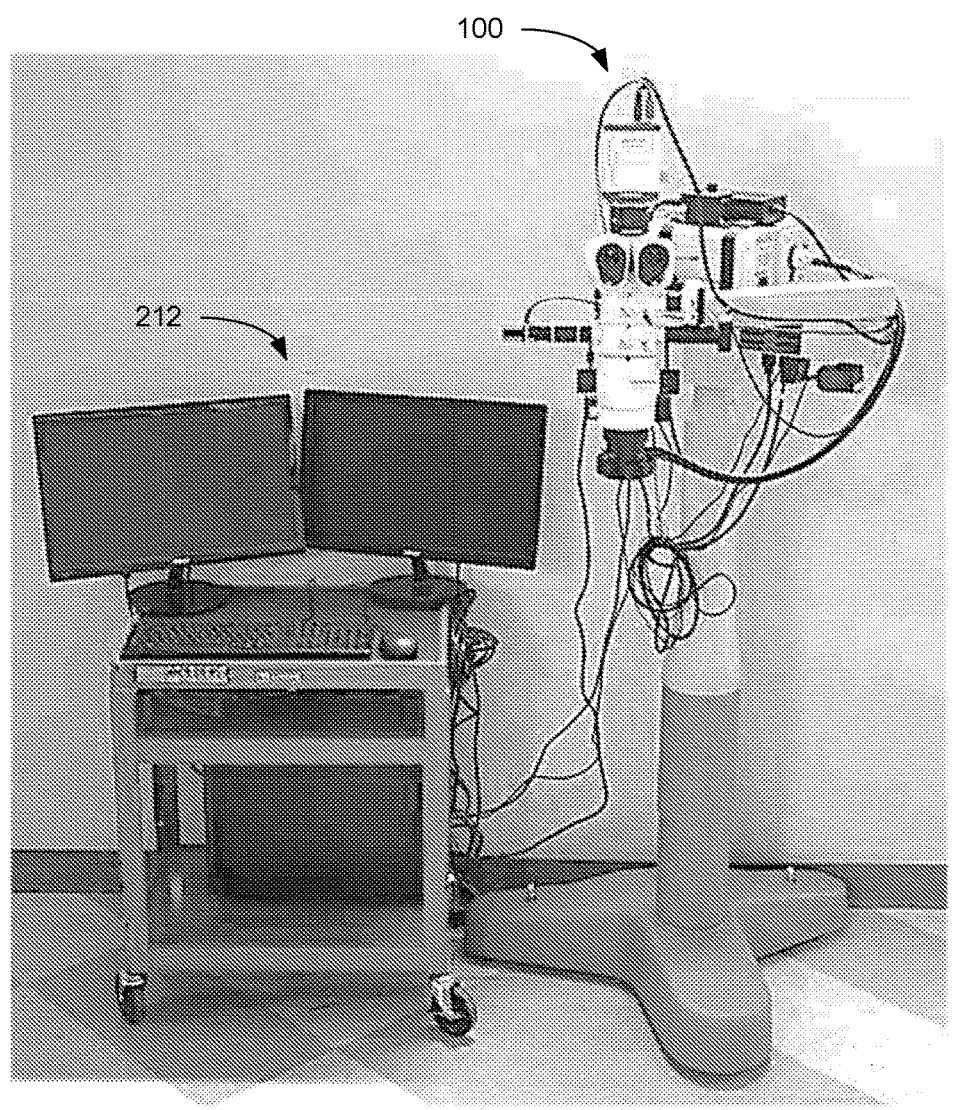

Disclosed herein are various examples related to imaging with augmented stereoscopic microscopes. This disclosure is not limited to particular embodiments described, and as such may, of course, vary. The terminology used herein serves the purpose of describing particular embodiments only, and is not intended to be limiting.

Preservation of blood flow in normal vasculature and exclusion of flow from vascular lesions are important concepts of neurosurgery. Even minimal compromise of vessel lumens can cause ischemic changes; conversely, residual flow into a vascular malformation can maintain the catastrophic risk associated with rupture. Several methods can be used for intraoperative assessment of blood vessel patency. Intraoperative digital subtraction angiography (DSA) can be implemented in complex vascular cases. Based on DSA results, 7-34% of cases may need additional manipulation to restore optimal blood flow. While DSA is considered the gold standard for vascular imaging, it utilizes substantial resources, including additional time and staff to perform the procedure. Intraoperative Doppler ultrasound and flowmetry may also be effective for detection of major vessel stenosis after aneurysm clip placement. However, these techniques do not have high accuracy and only provide an indirect assessment of vessel lumen compromise.

Fluorescence angiography with fluorescein sodium and indocyanine green (ICG) was introduced for neurovascular procedures in the 1960s. Fluorescence angiography was used for observation of vessels on the brain surface; static images were captured and analyzed after surgery. Video angiography uses fluorescence excitation sources and filters integrated into the operative microscope to allow acquisition of multiple video loops that can be analyzed intraoperatively. Observation of a fluorescent contrast agent introduced into the vasculature allows assessment of local blood flow dynamics. Multiple clinical trials have shown the effectiveness of fluorescence angiography in the management of vascular pathologies of the brain and spinal cord.

ICG video angiography can be acquired as video loops on an integrated camera after switching the white light optics to a near-infrared (NIR) filter set. Light from the field is directed to the camera, and, with the exception of some small background bleed through, the NIR image contains only fluorescence emitted from the ICG while the white light image is recorded independently. With sufficient contrast, the angiographic image can be added in real time back to the white light image seen in the oculars. In such fluorescence angiography with augmented microscopy enhancement (FAAME), the relationship between the angiographic data and the rest of the tissue or instrumentation can be directly visualized rather than inferred. Here, various realizations are discussed for combinations of FAAME and real-time observation of NIR fluorescence angiography augmenting the conventional white light field of view within the oculars of the operating microscope. These realizations can be expanded to include real time visualization features.

In addition, a limitation to current surgical cancer treatment is boundary delineation, and accurately identifying tumor margins remains of paramount importance during surgical resection of cancerous tissue. Superior vascularization of malignancies, and increased vascular permeability compared to normal vessels, can provide for increased uptake of exogenous contrast agents within the tumor tissue compared to surrounding normal tissue. NIR fluorescent contrast agents are desirable for biomedical imaging purposes due to their ability to uptake into tumor tissue and improve contrast at the tumor margins. The use of NIR emitting dyes allows for increased depth penetration and detection with minimal interaction with biological tissue. ICG is commonly used for video angiography, and several other NIR dyes may be used for delineation of a brain tumor or other biological features.

In medical applications, augmented imaging can be employed to deliver a variety of diagnostic information, whether prerecorded or acquired in real time, which can be merged with real images of the surgical field. Various types of synthetic images, such as those generated using electronically stored data, can enhance performance of diagnostic and therapeutic procedures. These can include prerecorded information such as, but not limited to, magnetic resonance imaging (MRI), computed tomography (CT), or positron emission tomography (PET) scans. Synthetic images can also be acquired and displayed in real time. These can include, e.g., thermal images obtained from thermal cameras or various fluorescence detectors such as, but not limited to, fluorescence intensity decay and/or polarization in the visible, near infrared and/or ultraviolet ranges. The composite images can aid the surgeon in making more accurate decisions and thereby improve tumor resections or other treatments.

Neurovascular surgery often utilizes surgical microscopes for better visualization and image guidance. Neurosurgical microscopes can include an optional attachment for acquisition of NIR fluorescence images of ICG. However, this secondary imaging modality is performed via a switchable technique where bright-field and NIR imaging are separate modalities. The lack of real-time co-registration can add time and uncertainty to procedures guided by NIR fluorescence. Therefore, to allow for simultaneous bright-field (real) and NIR (synthetic) imaging within the ocular of the microscope, an augmented microscope can be used to improve image guidance during surgical intervention.

An augmented microscope can produce a simultaneous view of the real anatomy (real object) and one or more computer-processed synthetic object (e.g., near-infrared fluorescence), which can be superimposed in real time, while maintaining their spatial co-registration. Examples of synthetic objects of interest to a neurosurgeon include stereotactic coordinates, single-point analytical data such as the temperature or oxygen concentration, distribution of a NIR fluorescent disease marker, and/or location of a NIR surgical laser beam. The composite image (representing a mixed or augmented reality) can be displayed in standard binocular configuration and presents a user-controlled balance of features of interest. Augmented microscopy, capable of displaying these markers in real time and superimposed with anatomical images of the operative field, may improve surgical efficiency and help guide surgical procedures, deliver therapies, and improve resection of tumors.

Embodiments of the present disclosure discuss systems and methods for augmented stereoscopic microscopic imaging. In one embodiment, among others, an augmented stereoscopic microscope comprises an objective lens configured to simultaneously receive near infrared (NIR) images and visible bright-field images of an examined object. The augmented microscope includes an augmentation module configured to separate the NIR images from the visible bright-field images for processing by an image processing unit to produce synthetic images based upon the NIR images. The augmentation module combines the synthetic images with the visible bright-field images to form co-registered augmented images that are directed to an eyepiece of the augmented stereoscopic microscope. The augmentation module can be configured to form co-registered augmented images for a right optical path and for a left optical path of the augmented stereoscopic microscope. The synthetic images can comprise visible pseudo-color images (e.g., visible green images). The synthetic images can include one or more additional synthetic objects for display in the augmented images.

In one implementation, the augmentation module comprises a beamsplitter (e.g., a dichroic beamsplitter) configured to combine the synthetic images with the visible bright-field images to form the co-registered augmented images. The synthetic images can be projected onto the beamsplitter to overlay the visible bright-field images. In another implementation, the augmentation module comprises a spatial light modulator such as a micromirror array configured to combine the synthetic images with the visible bright-field images to form the co-registered augmented images. At least a portion of the micromirror array can be switched to reflect at least a portion of the synthetic images and at least a portion of the visible bright-field images. Portions of the micromirror array may be set (e.g., held in a fixed position) to continuously reflect a portion of the visible bright-field images and/or a portion of the synthetic images. Various types of micromirror arrays may be utilized. For example, a mechanical type (e.g., MEMS) or an electronic type (e.g., a liquid crystal or electro-switchable mirror or other controllable mirror with no moving parts). Positioning of the mirrors in the micromirror array can be set for the appropriate reflection.

The augmentation module can comprise a light emitting diode (LED) configured to illuminate the object with NIR excitation light via the objective lens. The augmentation module can also comprise a sensor that is configured to capture the NIR images. The sensor may also capture the visible bright-field images and/or the co-registered augmented images. In some embodiments, a separate sensor can be used to capture the visible bright-field images and/or the co-registered augmented images. The augmentation module can also comprise a short-pass filter to remove NIR light from the co-registered augmented images that are directed to the eyepiece of the augmented microscope.

In another embodiment, a method comprises obtaining a near infrared (NIR) image of an examined object; generating a synthetic image based upon the NIR image; combining the synthetic image with a real-time visual image of the examined object to form an augmented image; and directing the augmented image to an eyepiece of an augmented stereoscopic microscope. The examined object can be illuminated with NIR excitation through an objective lens of the augmented stereoscopic microscope. In some cases, the examined object includes a NIR laser. In one implementation, the synthetic image can be projected onto a beamsplitter to overlay the real-time visual image. In another implementation, at least a portion of a micromirror array can be switched to reflect at least a portion of the synthetic image and at least a portion of the real-time visual image. The synthetic image can comprise a chemical concentration in the examined object and/or a temperature of the examined object. Reference will now be made in detail to the description of the embodiments as illustrated in the drawings, wherein like reference numbers indicate like parts throughout the several views.

Referring to FIGS. 1A and 1B, shown is an example of an augmented microscope 100 mounted on a surgical stand. The augmented microscope 100 can integrate in real time electronically processed near-infrared (NIR) images (or synthetic objects), with visible (VIS) images (or real objects) obtained utilizing an augmentation module inserted into a conventional microscope configuration. This can be accomplished using an optical see-through display technology, which allows real and synthetic images to be superimposed for viewing. The resultant composite image, which can also be referred to as an augmented reality, can be displayed in a standard binocular configuration and represents a user-controlled balance of features of interest.

In the example of FIGS. 1A and 1B, the augmented microscope 100 was constructed using a commercial stereomicroscope (e.g., Olympus SZX7, Center Valley, Pa.). Galilean optics employed in the microscope 100 includes two (left and right) parallel optical paths, in which modular units can be inserted for desired functionalities. As illustrated in FIG. 1B, the augmented microscope 100 can include a CMOS (complementary meta-oxide semiconductor) or a CCD (charge-coupled device) sensor 103 (e.g., a camera), LED (light emitting diode) excitation 106, an augmentation module 109, a metal halide ring illuminator 112, an OLED (organic LED) projector 115, and/or an eyepiece camera 118. In some implementations, a NIR module can be included for simultaneous and independent acquisition of visible (VIS) and NIR images.

The augmentation module 109 can accommodate fluorescence excitation and detection hardware and an image projection system. NIR fluorescence can be excited using, e.g., a 420 mW 780 nm diode (e.g., LEDD1B, Thorlabs, Newton, N.J.), and detected using the CMOS sensor 103 (e.g., a camera such as an ORCA-Flash4.0, Hamamatsu, Hamamatsu City). In any embodiment of this disclosure, the sensor 103 can be a camera including CMOS, CCD, or other appropriate technologies. The fluorescence image can then be projected back into the optical path of the microscope 100 as a pseudo-color image via an OLED projector 115 (e.g., Green OLED-XL, eMagin, Bellevue, Wash.) and a 50/50 beamsplitter. In other implementations, projectors other than OLED can be used, including Digital Light Processing (DLP), Liquid Crystal Display (LCD) or Liquid Crystal on Silicon (LCoS) technologies. In some implementations, proper co-registration can be preserved by capturing and projecting the NIR fluorescence all within the optical path of the microscope 100. This allows for real-time visualization of the composite images within the ocular of the microscope 100. The metal halide ring illuminator 112 (e.g., Fiber Lite MH-100, Dolan-Jenner Industries, Boxborough, Mass.) can be used for bright-field illumination and the optional eyepiece camera 118 may be mounted to the microscope 100 for real-time recording of the composite image seen in the ocular.

Referring to FIG. 2, shown is a schematic representation of an example of an optical scheme for the augmented fluorescence microscope 100. The light 203 from a high power NIR LED 106 (e.g., with radiation power of 350 mW or higher) can be inserted into the microscope optical path using a dichroic mirror. For example, light from the high power LED 106 can be centered at 780 nm for ICG excitation. The resulting NIR fluorescence image 206 can be separated from the optical path of the microscope by a NIR band pass filter (e.g., matching the emission range of ICG). The NIR fluorescence images 206 can be captured by the NIR CCD or CMOS camera (or sensor) 103 with extended sensitivity in near infrared and converted into visible green pseudo-color images 209 using an image processing station 212 and a monochromatic OLED projector 115. Light intensity produced by the OLED is representative of the fluorescence emission intensity captured by the CMOS sensor 103. The OLED projector 115 projects the pseudo-color images 209 onto a half-mirror placed in the ocular of the microscope 100, where the processed (synthetic) image 209 overlays with the original (real) visible light image 215 from the objective lens 218 to produce augmented, or composite, images. Operation of the NIR path described above retains the original path of the visible image 215 within the microscope 100, with minimal losses due to the half-mirror.

In addition, this augmented system can provide the capability to observe traditional fluorescence images on a monitor screen (e.g., of image processing station 212). Images can be projected onto the monitor in real-time, or retrospectively from the saved video file(s). Images can be projected on the monitor screen in a visible (VIS), NIR, and/or an augmented format. All visual formats can be collected simultaneously, but may be displayed separately (e.g., VIS or NIR only) or in combination (augmented) as desired. Fluorescence excitation and recording can be under user control, allowing it to be turned on and off as appropriate.

Figure 3:
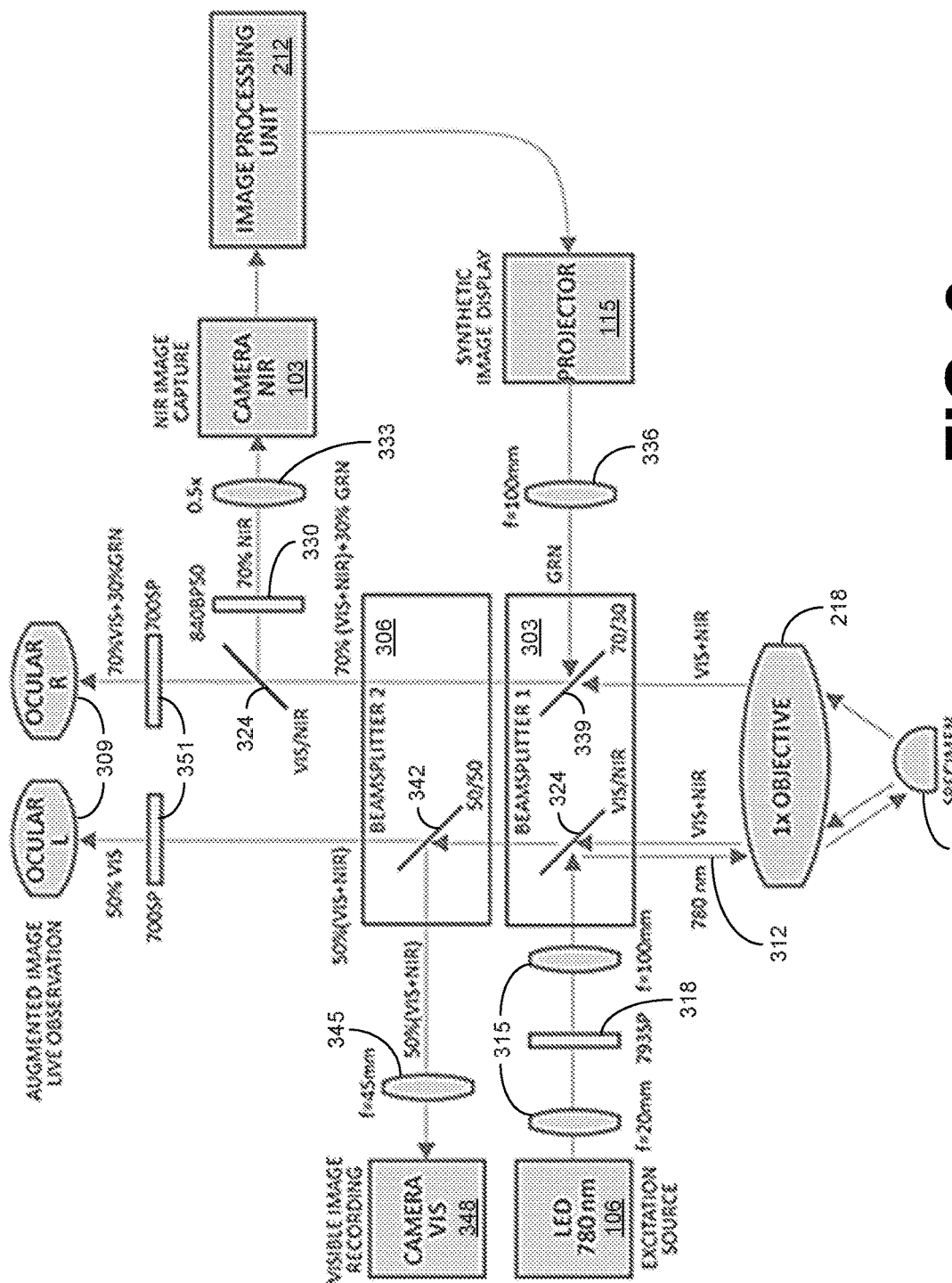

Referring to FIG. 3, shown is an example of single channel augmentation of a stereoscopic microscope. The optics of a standard stereomicroscope can be configured for the augmented microscopy functions by inserting additional augmentation modules in its light paths. As shown in FIG. 3, two augmentation modules 303 (beamsplitter 1) and 306 (beamsplitter 2) are included in the light paths between the objective 218 and the ocular lenses 309. The example of FIG. 3 overlays a fluorescence image of ICG onto the optical image of the same field of view. Excitation light can be provided by a 780 nm LED 106, with the excitation beam 312 formed using two lenses 315 (e.g., f=20 mm and f=100 mm). A short pass filter 318 (e.g., 793SP) can be introduced to remove long wavelengths from the excitation beam 312. The excitation beam 312 can then be directed toward the sample or specimen 321 using a dichroic beamsplitter 324 (VIS/NIR).

The NIR fluorescence image can be acquired through a dichroic beamsplitter 327 (VIS/NIR) placed before, e.g., the right ocular lens 309. The fluorescence emission is separated using a band pass filter 330 (e.g., 840BP50) and captured using an image forming lens 333 (e.g., 0.5×) and a NIR-sensitive scientific CMOS camera 103 (NIR CAMERA) such as, e.g., an Orca Flash 4.0. Subsequently, the NIR image can be processed by the imaging processing unit 212 to obtain the desired field of view, contrast, brightness, and/or feature extraction. In the example of FIG. 3, a synthetic image in green (GRN) is projected by a miniature OLED projector 115 through an image forming lens 336 (e.g., f=100 mm) and onto a beamsplitter 339 (e.g., T/R: 70/30) to form the composite image in the right ocular lens 309. For image recording purposes, a beamsplitter 342 (e.g., T/R: 50/50) can be placed in, e.g., the left channel and the visible image can be captured using an image forming lens 345 (e.g., f=45 mm) and a CMOS camera 348 (CAMERA VIS). A set of short-pass filters 351 (e.g., 700SP) can be introduced before ocular lenses to block any remaining NIR light.

Utilizing the single channel augmentation of FIG. 3, the co-registration of the composite images performed in real time and superior to current clinical practice where the clinician switches between the visible and the NIR channels. With the real time augmentation, no switching is necessary. Image settings can include visible and NIR intensity, contrast/brightness, and/or color correction, which can be adjusted in real time for optimum image acquisition, feature identification, and user preference. While the example of FIG. 3 illustrates augmentation of the right channel, it can be understood that augmentation of the left channel can be carried out in a similar fashion.

In some implementations, synthetic images other than that produced by the NIR camera (or sensor) 103 can be combined with the visible bright-field images by projecting the synthetic images onto the beamsplitter 303 to overlay the visible bright-field images. For example, the image processing unit 212 and projector 115 can be used to overlay prerecorded information obtained through MRI, CT, or PET scans of the examined object. Real-time synthetic images (e.g., chemical concentration or thermal images obtained from thermal cameras or various fluorescence detectors such as, but not limited to, fluorescence intensity decay and/or polarization in the visible, near infrared and/or ultraviolet ranges can also be acquired and displayed over the visible bright-field images using the image processing unit 212 and projector 115.

Figure 4A:
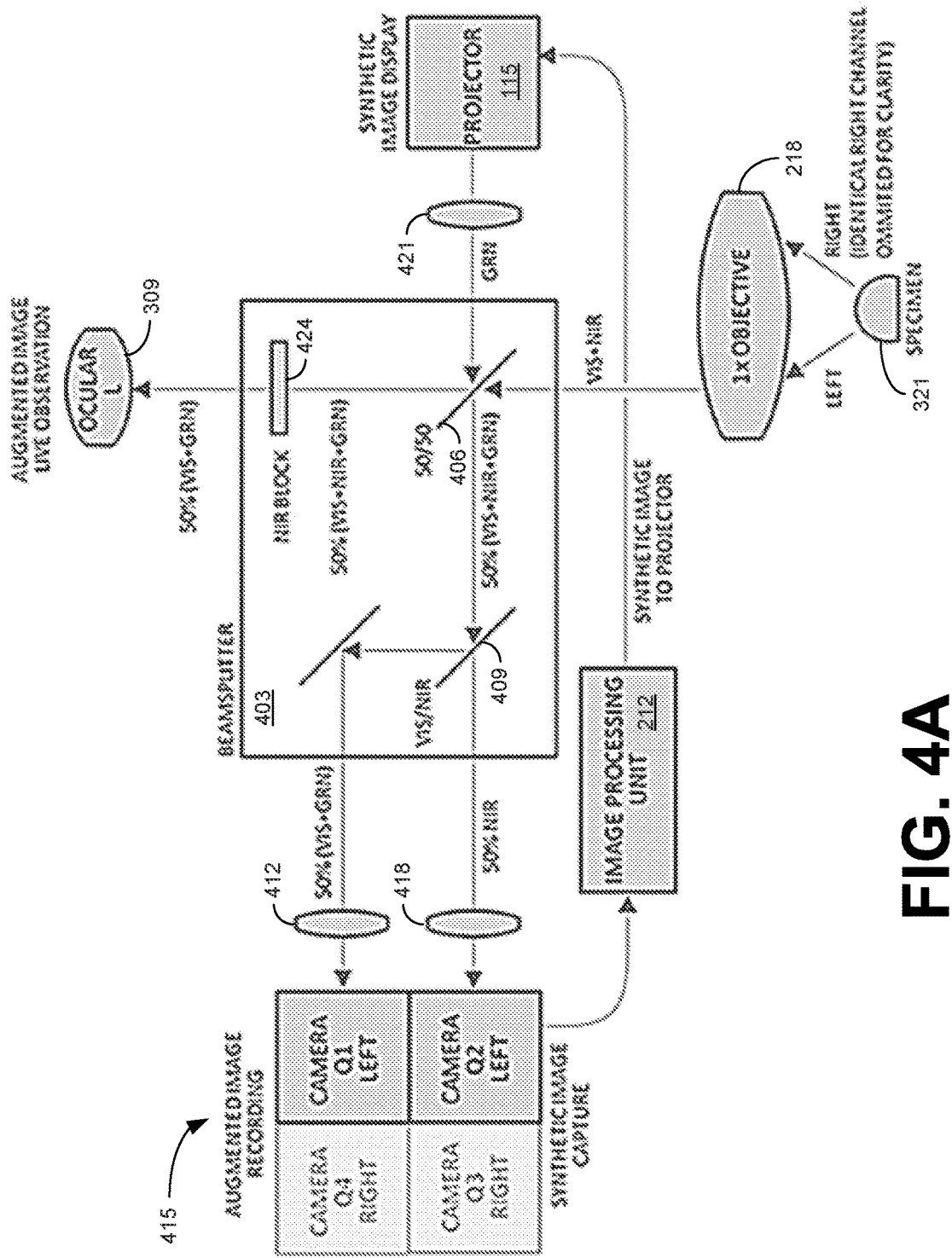
Figure 4B:
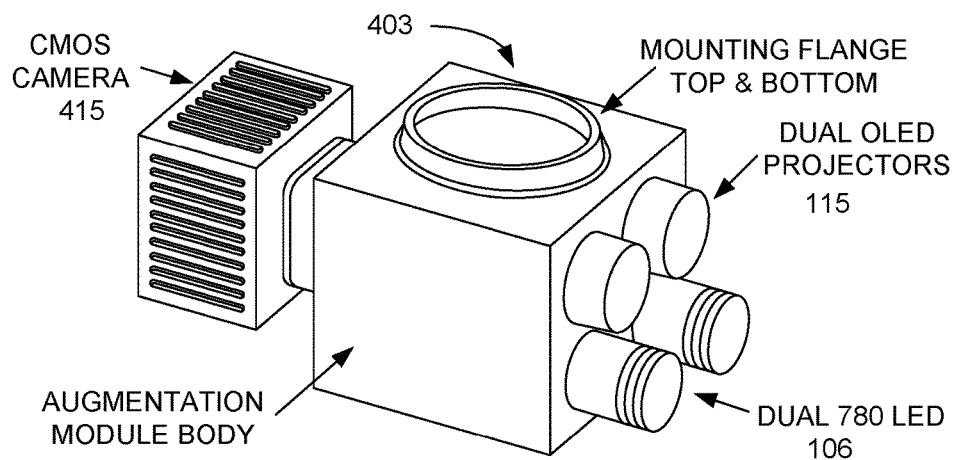
FIG. 4B is a perspective view of an example of an augmentation module of FIGS. 4A and 4C in accordance with various embodiments of the present disclosure.
Figure 4C:
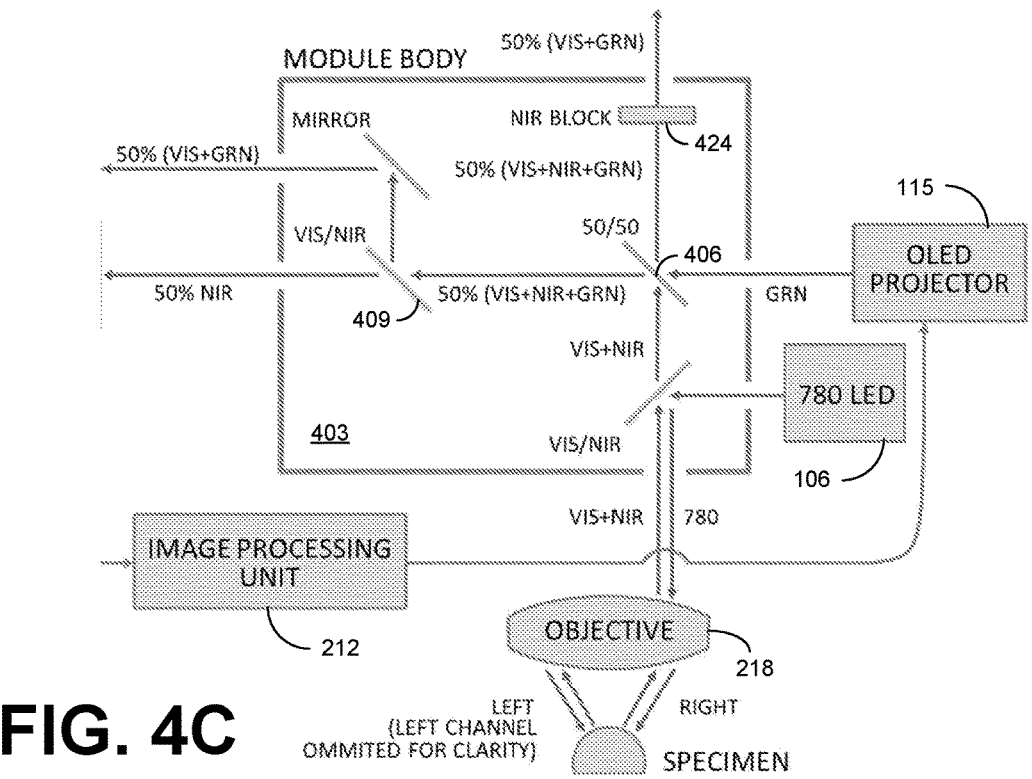

Referring to FIGS. 4A through 4C, shown is an example of dual channel (or full) augmentation of a stereoscopic microscope. The optics of a standard stereomicroscope can be configured for the augmented microscopy functions by inserting additional augmentation modules in its light paths. The example of FIGS. 4A-4C overlays a fluorescence image of ICG onto the optical image of the same field of view. As shown in FIGS. 4A and 4C, an augmentation module 403 is included in the light path between the objective 218 and the ocular lens 309. In FIG. 4A, only the left channel is illustrated for clarity, but the same configuration can be used for the right channel.

Near infrared (NIR) fluorescence and visible (VIS) images can be acquired through a beamsplitter 406 (e.g., T/R: 50/50) in the augmentation module 403. The visible (VIS) image can be separated using a dichroic beamsplitter 409 (VIS/NIR) and captured using an image forming lens 412 and, e.g., a first quadrant (Q1) of a scientific CMOS camera 415. The NIR fluorescence emission can be separated using the same dichroic beamsplitter 409 and captured using an image forming lens 418 and, e.g., the second quadrant (Q2) of the scientific CMOS camera 415. Subsequently, the NIR image can be processed to obtain the desired field of view, contrast, brightness, and/or feature extraction.

In the example of FIGS. 4A and 4C, a synthetic image in green (GRN) is projected using a miniature OLED projector 115 and an image forming lens 421 onto the 50/50 beamsplitter 406 to form the composite image in the ocular lens 309. Note that in the configuration of FIG. 4A, the visible image collected in the first quadrant Q1 of the CMOS camera 415 includes the exact copy of the augmented image (VIS+GRN) as seen by the operator. A short-pass filter 424 (700SP) is introduced before ocular lens 309 to block any remaining NIR light. In the configuration of FIG. 4A, excitation light (780 nm) for excitation of ICG fluorescence can be introduced by an objective-mounted ring illuminator.

The augmentation module 403 enables a live acquisition of the augmented images as seen by the operator, for record keeping or real-time display. A fully augmented optical stereoscopic image retains characteristics enabling proper three-dimensional perception. As a result, anatomical features and spatial orientation can be provided by the real image whereas synthetic image adds diagnostic features with the proper spatial co-registration of the left and right channels, so that both the real and synthetic images appear in the same axial and lateral positions.

As illustrated in FIG. 4A, the objective 218 captures both visible light (VIS) carrying anatomical features and near infrared (NIR) carrying diagnostic information. The augmentation module 403 is positioned between the microscope body and the eyepieces, in a manner similar to standard beamsplitters. However, the augmentation module 403 can have several dedicated ports not available on standard beamsplitters. FIG. 4B is a perspective view illustrating an example of the augmentation module 403 that can be placed between the microscope body and the eyepiece, using a standard flange system. A quadruple port can be designed for capturing multiple images with a single CMOS sensor (or camera) 415. The four-quadrant CMOS camera 415 can capture NIR images for the left and right channels can be captured to produce the synthetic stereoscopic images, while the augmented images can be simultaneously captured for the left and right channels to provide a copy of what the observer sees in the eyepieces. Also, the augmentation module 403 can include a dedicated dual port for projecting the stereoscopic synthetic images into the optical path of the microscope via dual OLED projectors 115.

Dual 780 nm LED 106 (e.g., with radiation power of 350 mW or higher) can be used to provide excitation for fluorescence of near infrared dyes or agents, such as ICG. FIG. 4C illustrates an arrangement of the augmentation module 403 that allows excitation light provided by the 780 nm LED 106 to illuminate the sample or specimen through the objective 218. One or more image forming lenses can be positioned between the OLED projector 115 and beamsplitter 406, one or more collimating lenses can be placed in front of the 780 nm LED 106, and/or a prism system can be included for projecting four separate images onto the four quadrants of the CMOS sensor 415 (FIG. 4A). A short pass filter can also be introduced to remove long wavelengths from the excitation beam.

Excitation light can be directed to the specimen using a dichroic bandpass mirror 406 that can reflect light in a range of 720-790 nm and transmit light in both the 400-700 nm (visible range) and 800-900 nm (near infrared range) ranges. Returning NIR emissions will be split 50/50, for direct viewing in the eyepieces and toward the camera. The independent addressing of subarrays, characteristic of the CMOS architecture, allows the four VIS and NIR images to be acquired on one sensor. Independent control of exposure time and readout rate can be used to compensate for differences in photon fluxes in the visible and near-infrared spectral ranges. For example, a CMOS camera 415 such as a Hamamatsu Orca Flash 4.0 provides high resolution (4 megapixel) while being sensitive in the near-infrared, and maintaining a readout rate of up to 100 fps (frames per second) at full resolution. The near-infrared images can be processed for contrast, brightness, and/or thresholding, and then projected back into the optical path of the augmentation module 403 using two OLED projectors 115 (left and right channel). For example, a 0.78" diagonal, 5:4 aspect ratio, 1280×1024 pixel SXGA green monochrome projector (eMagine, Bellevue Wash.) can be used to provide the processed imaging. It can provide a luminance of 1500 $cd/m^2$ with good contrast within a typical color pallet of a surgical field of view. The acquired images can be captured and stored onto, e.g., a solid state disk. A variety of image processing routines from ImageJ libraries, and Matlab or C++ for Graphic User Interface can be used.

In some implementations, synthetic images other than that produced by the NIR camera (or sensor) can be combined with the visible bright-field images by projecting the synthetic images onto the beamsplitter 403 to overlay the visible bright-field images. For example, the image processing unit 212 and projector 115 can be used to overlay prerecorded information obtained through MRI, CT, or PET scans of the examined object. Real-time synthetic images (e.g., chemical concentration or thermal images obtained from thermal cameras or various fluorescence detectors such as, but not limited to, fluorescence intensity decay and/or polarization in the visible, near infrared and/or ultraviolet ranges can also be acquired and displayed over the visible bright-field images using the image processing unit 212 and projector 115.

A variety of tests have been carried out to illustrate the efficacy of the augmented microscope 100 with regard to NIR imaging using ICG. A stock ICG solution (Cardio green, Sigma Aldrich, St. Louis, Mo.) was prepared by dissolving 4.8 mg/mL ICG (6.19 mM) in a 60 g/L bovine serum albumin (BSA) solution with phosphate buffered saline (PBS). The stock solution was serially diluted with 60 g/L BSA with PBS for imaging, ensuring the BSA concentration remained constant while diluting the ICG. The ICG solution was used within 6 hours of preparation. A concentration of 194 µM was expected to produce maximal fluorescence intensity.

Figure 5:
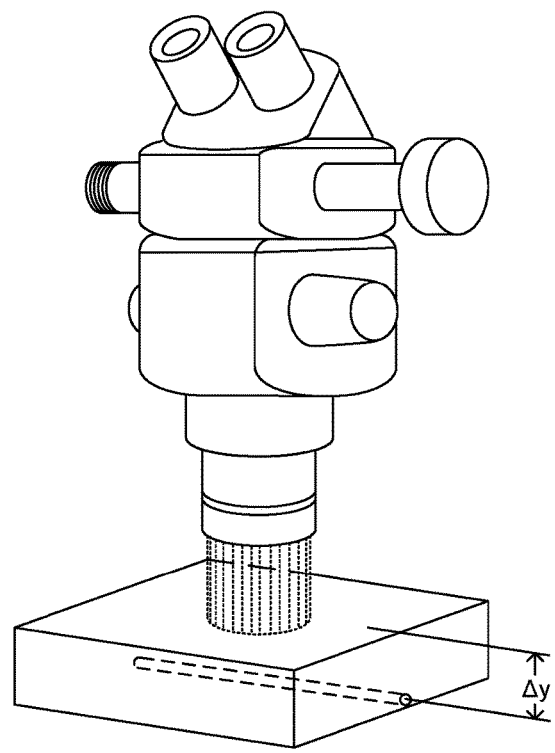
FIG. 5 is a schematic representation illustrating the augmented microscope of FIGS. 1A and 1B in position to image a sample or specimen in accordance with various embodiments of the present disclosure.

FIG. 5 is a schematic representation illustrating the augmented stereoscopic microscope 100 in position to image a tissue phantom with capillary tube placed at depth equal to Δy. The CMOS sensor 103 (FIG. 1B) was set to a 50 ms exposure time (approximately 20 frames per second) for real-time video recording. The total magnification was variable from 8×-56× with an installed 1× NA 0.10 objective lens 218 (FIG. 2). Metal halide output was set to maximum producing 80,000 Lux, and NIR excitation was set to maximum output. Bright-field, NIR, and composite images were captured and saved for further review and/or processing.

Initially, polyacrylamide tissue phantoms were prepared with integrated polystyrene beads (e.g., 1.530±0.039 µm, Polybead® microspheres, Polysciences Inc, Warrington, Pa.) to simulate optical properties similar to natural brain tissue. The gels were prepared with one sphere per 1100 µm3, which gave a $\mu_s=30$ cm$^{-1}$. The phantoms were made with different thicknesses ranging from 1-8 mm using a custom 3D printed cast. An online calculator was used to calculate the percentage of polystyrene beads to obtain an appropriate scattering coefficient.

Glass capillary tubes (about 1 mm in diameter) were embedded in the tissue phantom to image ICG at varying depths as illustrated in FIG. 5. To evaluate the sensitivity of the augmented microscope 100, tissue phantoms were imaged as follows: 1) imaging ICG serial dilutions in capillary tubes directly, and 2) imaging ICG serial dilutions in capillary tubes under tissue phantoms. The resolution of the augmented microscope 100 was determined via imaging of an air force target. The Albert Rose criteria were used to determine sensitivity via signal-to-noise ratio (SNR).

Figure 6A:
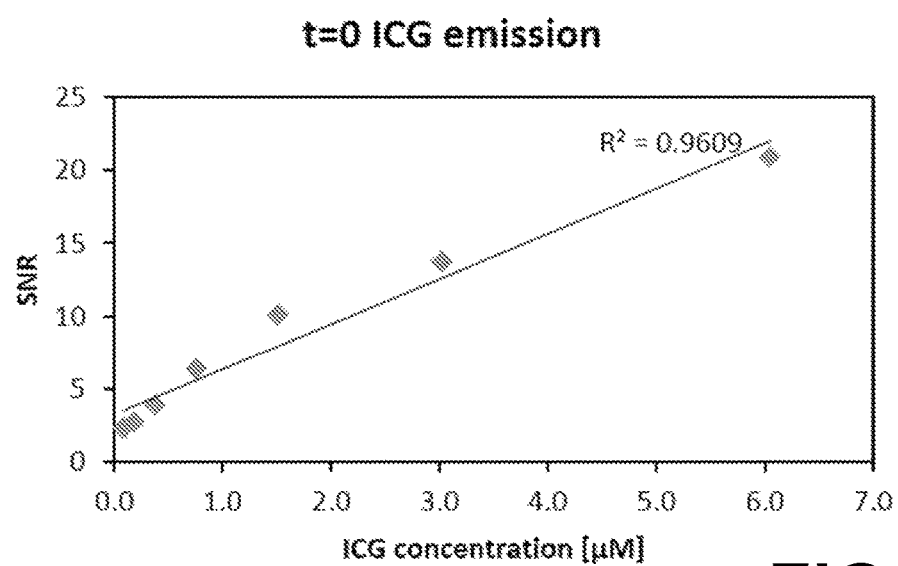
FIGS. 6A and 6B are plots illustrating the fluorescence imaging sensitivity of the augmented microscope of FIGS. 1A and 1B in position to image a sample or specimen in accordance with various embodiments of the present disclosure.
Figure 6B:
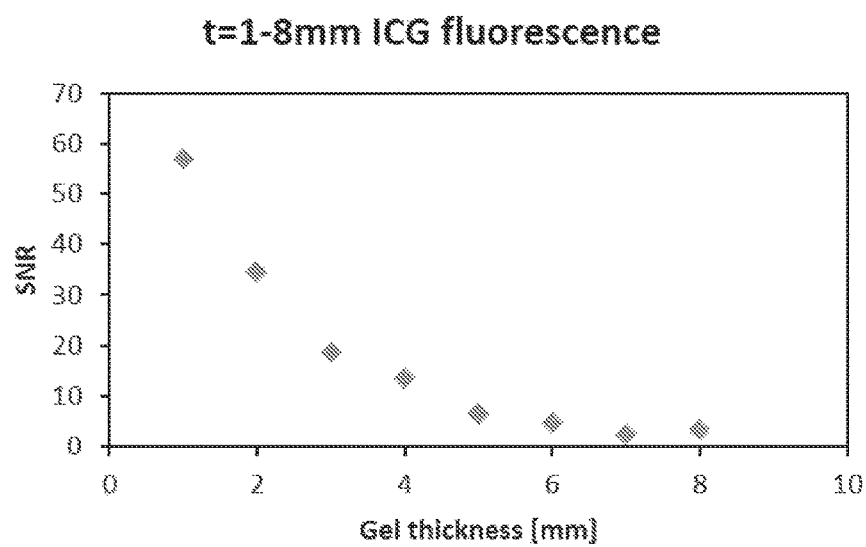

The augmented microscope 100 was capable of resolving group 6, element 7 on the air force target. The augmented microscope 100 was also able to resolve a minimal ICG concentration of 94.5 nM with an SNR of 2.3. The maximal fluorescence signal was obtained with ICG concentration of 194 µM, which was consistent with earlier work. Referring to FIGS. 6A and 6B, shown are plots illustrating the fluorescence imaging sensitivity of the augmented microscope 100. FIG. 6A shows the serial dilution imaging of ICG in the capillary tubes directly. The fluorescence intensity had a linear relationship (R2=0.9609) between 94.5 nM to 6.05 µM, where signal intensity flattened off between 6.05 µM to 194 µM. A decrease in intensity was observed beyond 194 µM, which may be attributed to concentration dependent fluorescence quenching. FIG. 6B shows the imaging of the 194 µM ICG in the capillary tube at increasing depths from 1 mm to 8 mm in tissue phantoms. In this model, a 194 µM solution of ICG was detectable up to depths of 5 mm.

The augmented microscope 100 was also used for in vivo imaging to evaluate its ability to produce augmented images in real time. A Sprague Dawley rat model (300 g, n=5) was used to demonstrate in vivo video angiography using the augmented microscope 100. The rats were anesthetized with intramuscular injection of a ketamine/zylazine/acepromazine cocktail. The left carotid artery was exposed via a microsurgical technique under the augmented microscope 100. The 0.3 mL of 0.6 mg/mL ICG solution (774 µM) was injected and the left carotid artery imaged.

Figure 7:
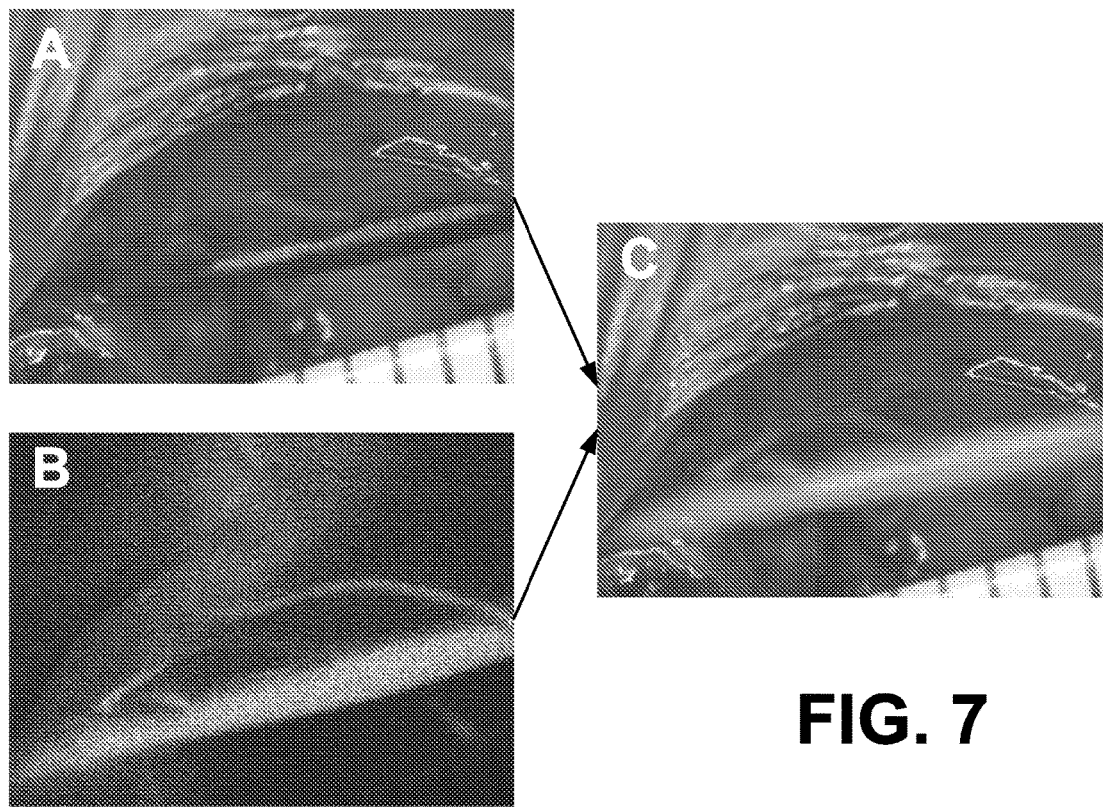

The images of FIG. 7 illustrate the in vivo imaging with the augmented microscope 100. Visible, NIR, and augmented images (A, B, and C respectively) were captured from video angiography. ICG fluorescence was visualized in the left carotid artery and used to produce the augmented image C, which exemplifies the exact view through the ocular of the augmented microscope 100 in real time. Co-registration was retained throughout imaging with variable magnification and focusing. The working distance was approximately 100 mm with a field of view ranging from 27.5-3.9 mm. The augmented imagery showed excellent balance between colors and intensity with substantial fluorescence overlay indicating the location of the ICG dye. The fluorescence was observed within the vessel boundaries with user-controlled balance between bright-field and fluorescence overlay. User defined optimization of the composite image C enables simultaneous observation of the surgical field and weak fluorescence of contrast agents or high power NIR laser beams for laser surgery, or any other type of computer-generated images.

FAAME maintains full direct stereoscopic visualization of white light anatomy in conjunction with the ICG angiogram, which is viewed as a pseudocolored overlay. The process of device calibration was simplified using in vitro images of glass tubes filled with saline and ICG solutions, allowing the image acquisition parameters to be optimized. In order to calibrate the augmented microscope 100, proper co-registration of the on lay fluorescence image with the real-time white light image was ensured to reproduce shapes and sizes of test objects. Once calibration was set with initial image, further adjustments of the augmented microscope 100 were not needed for consecutive imaging.

FAAME experiments were then performed to assess the feasibility of the augmented microscope 100 to perform ex vivo video angiography. Turkey wing brachial arteries (n=3) were dissected using a microsurgical technique. The proximal ends of the exposed vessels were transected for cannulation. A 16-gauge cannula was inserted into the proximal vessel lumen and secured with a silk tie. The cannula was connected to an infusion system with a flow regulator and the infusion bag was filled with the ICG solution. The augmented microscope 100 was positioned above the vessel and FAAME was then initiated. The infusion of the ICG was initiated after a five-second delay. Using FAAME, the green image representing fluorescence emission was observed as dynamic flow overlaid with the visible vessel.

Examples of the ex vivo FAAME images of the turkey wing after ICG injection into brachial artery are shown in FIG. 8. Image A of FIG. 8 was obtained using the VIS (or white light) path only. The dissected brachial artery can be seen within the field of view. Image B of FIG. 8 was obtained using the NIR path only. The ICG fluorescence pattern delineates the anatomical boundaries of the brachial artery, while the surrounding anatomical structures are not visible. Image C of FIG. 8 was obtained by augmentation of the VIS image A with the NIR image B. The ICG fluorescence pattern and surrounding anatomical structures are readily visible within the field of view.

Additional in vivo experiments were also carried out. Three-month-old female Sprague Dawley rats (n=7) having an average body weight of 350 grams were anesthetized by an intramuscular injection of Ketamine/Xylazine/Acepromazine cocktail. The animals were placed supine and the femoral arteries and jugular veins were exposed using standard microsurgical technique under the augmented microscope 100. Wth the augmented microscope 100 positioned to image the femoral artery, FAAME was initiated.

Using a 1 cc syringe and a 30 gauge needle, 0.3 ml of 0.3 mg/ml ICG solution was injected under direct visualization into the jugular vein. A high contrast fluorescent signal was visible in the oculars presenting a dynamic pattern of real-time flow into the femoral artery and its branches. Video loops were recorded for further analysis. After completion of experiments, the animals were euthanized according to institutional guidelines.

Examples of the in vivo FAAME images of the femoral artery of the rat after ICG injection into jugular vein are shown in FIG. 9. Image A of FIG. 9 was obtained using VIS (or white light) path only. The exposed femoral artery (arrow 903) and femoral vein (arrowhead 906) are visible within the field of view. Image B of FIG. 9 was obtained using the NIR path only. The ICG fluorescence can be observed within anatomical borders of femoral artery, while the surrounding anatomical structures cannot be identified. Image C of FIG. 9 was obtained by augmentation of the VIS image A with the NIR image B. The anatomical structures within the field of view can be identified. The ICG fluorescence appears as a bright green signal within anatomical borders of the femoral artery. The segment of the femoral artery covered by fat and connective tissue is clearly delineated (arrow 909).

FAAME produced high contrast pseudo-colored real-time green angiograms of ex vivo and in vivo microvasculature samples. The overlaid ICG angiograms were not disruptive to the white light images and could be adjusted or eliminated on demand. They appeared as a bright green signal within anatomic boundaries of the vessel wall. The direction of flow of the angiogram confined within the vessels was accurate. Adjacent anatomical structures, e.g., skin, muscles, were also visible as with conventional surgical microscope. The segment of the artery covered by fat and connective tissue could be identified as well. During FAAME, at no point did the surgeon need to look away from the oculars or lose track of the view of the operative field. The ICG solution concentration and diameter of the vessels visualized (1.5 mm±0.3 mm) were consistent with common operative neurovascular conditions. The optics and electronics used are all amenable to integration with operating room microscopes.

Figure 10:
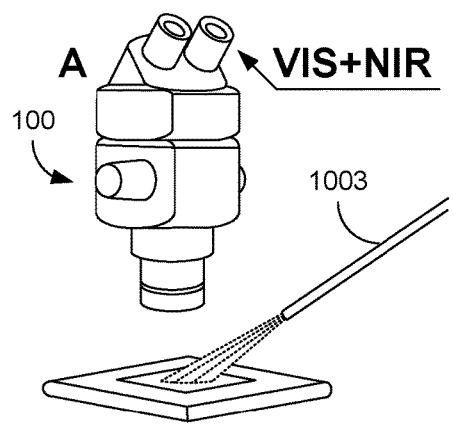
FIGS. 10-12 illustrate examples of use of a laser in conjunction with the augmented microscope of FIGS. 1A and 1B in accordance with various embodiments of the present disclosure.

The augmented microscope 100 can also enable visualization of NIR laser beams, such as those contemplated for photoactivated delivery of drugs, photothermal therapy, and/or laser surgeries. Referring to FIG. 10, shown is a 820 nm laser beam from a Ti:Sapph laser (Spectra-Physics MaiTai), which was delivered through a fiber optic probe terminated with a stainless steel wand 1003, a form factor frequently used for medical delivery of laser light. The laser beam was directed toward a target placed under the microscope as shown in image A of FIG. 10. Images B-D show a set of images acquired using an eyepiece camera, the operator can monitor a standard color image of the field of view (image B), an unprocessed NIR image of the laser beam (image C), or a composite image generated in the optical pathway of the augmented microscope 100, with a user-defined balance of the real scene and color-coded (green) NIR laser beam (image D). This capability allows for real-time overlay of the laser beam on the visual image B.

Figure 11:
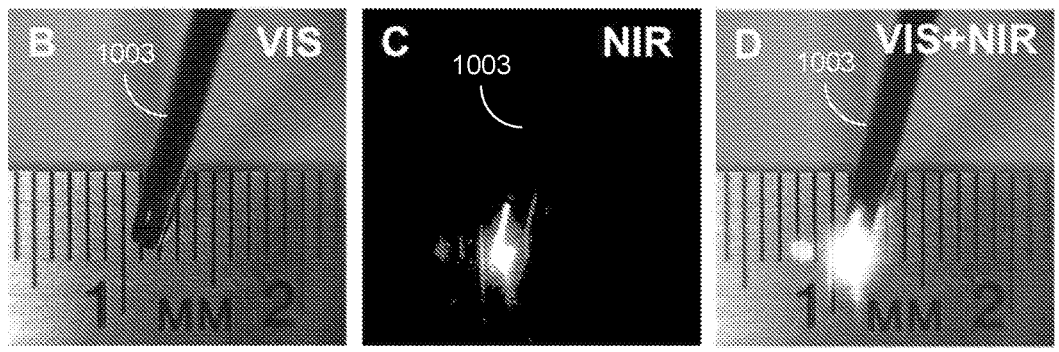
Figure 11:
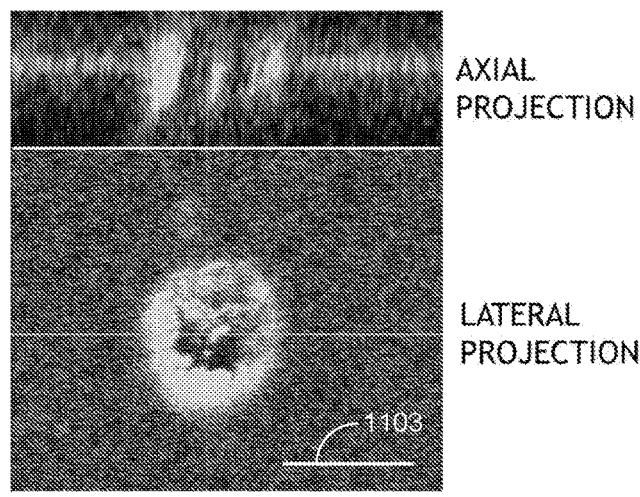

In addition to clinical angiography, the augmented microscope 100 can be used to guide a NIR laser beam in delivery of photothermal therapies, such as sensitized ablation of tissue for surgical resection of brain tumors. Referring to FIG. 11, shown is an example of photothermal ablation mediated by plasmon resonant nanoparticles of gold. Gold nanorods resonant at 780 nm were deposited on the polyacrylamide tissue phantom and illuminated at the resonant wavelength using a Ti-sapphire laser operating at 100 fs, 80 MHz. The spread of ablation in the hydrogel can be precisely controlled by selecting the area for laser illumination, forming a void as small as 20 µm, comparable with the size of individual cells. A selected spot of 5 µm×5 µm was irradiated with the scanning laser microscope using a resonant wavelength of 780 nm, 80 mW average power, and pixel dwell time 6.4 µs. FIG. 11 shows a 20 µm diameter crater that was formed using the laser illumination. Visualization of the 20 µm diameter crater was provided by multiphoton luminescence of gold nanoparticles. The bar 1103 is 20 µm.

Figure 12:
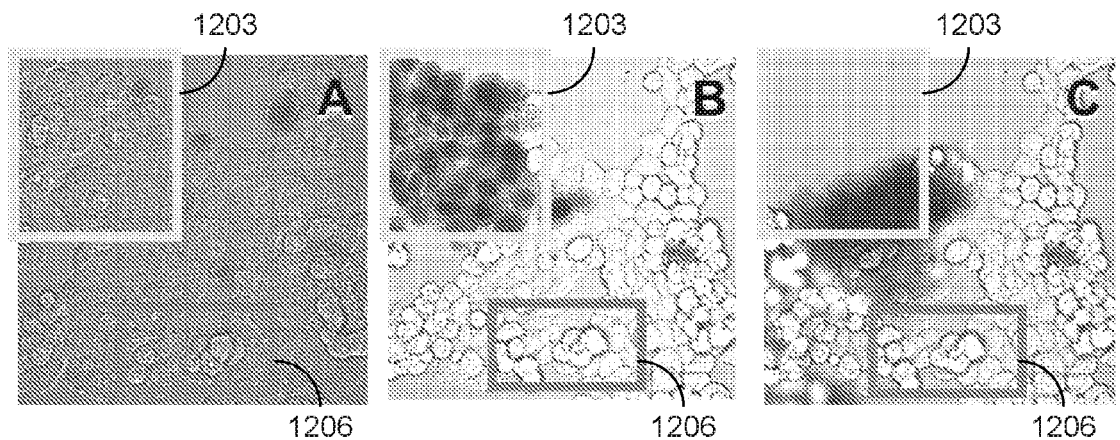

Cancer cells may be selectively eliminated using a similar combination of gold nanoparticles and femtosecond laser beam. Gold nanoparticles are sensitizers of the photothermal therapy. A section including spectrally tunable nanoparticles such as gold nanorods, gold nanoshells or others can be scanned with the NIR laser beam to eliminate the cancer, without incurring photothermal damage in areas without the tuned nanoparticles. Demonstration of a gold-nanoparticle-assisted laser photothermal treatment is illustrated in FIG. 12. In image A, two regions are selected for laser treatment: a region tagged with gold nanorods (box 1203) and a region with no nanorods (box 1206). Within 5 minutes of treatment, a majority of the cells tagged with gold nanorods were dead, as indicated by the dark trypan blue stain in box 1203 of image B. No change was observed in the irradiated non-nanorod region of box 1206 of image B. A subsequent wash of the system confirmed cellular damage in the nanorod-tagged region of box 1203 of image C of FIG. 12, where the affected cells were easily removed. The plasmon resonance of the gold nanoparticles when treated with a laser having the appropriate wavelength produces a lethal effect. The augmented microscope 100 allows the laser to be targeted to specific areas for treatment.

Figure 13:
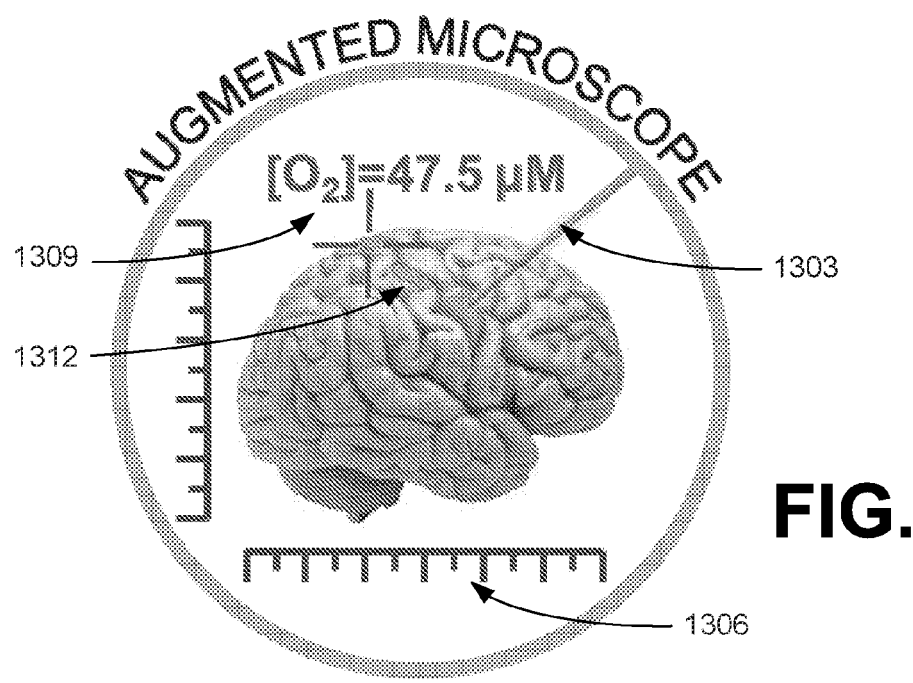
FIG. 13 illustrated an example of an optical view of the augmented microscope of FIGS. 1A and 1B in accordance with various embodiments of the present disclosure.

FIG. 13 is an example of a view that can be provided through the optics of the augmented microscope 100, where the location of a NIR surgical laser beam 1303 can be seen by the operator. The augmented microscope 100 can present a simultaneous view of real anatomy (real objects) superimposed with computer-processed data (one or more synthetic objects) while maintaining their spatial co-registration. Examples of synthetic objects of interest to a neurosurgeon can include stereotactic coordinates 1306, single-point analytical data such as the temperature and/or oxygen concentration 1309, or distribution of a near-infrared fluorescent disease marker 1312. The synthetic objects can be projected into the optical path of the microscope 100 via the OLED projector 115.

Luminescence imaging uses endogenous fluorescence or a luminescent (e.g., fluorescent) marker. A stereoscopic fluorescence image can be extracted by spectral filters from the anatomical image, enhanced and superimposed with anatomical image of the tissue. For augmented angiography, a NIR sensitive camera is used to display the distribution of a near-infrared fluorescent agent, ICG or similar, simultaneously with anatomical image of the tissue. For oxygen sensing, the augmented microscope 100 can include a time-gated camera that can be used to process luminescence quenching images of an oxygen-sensing luminescent dye into a quantitative map of distribution of the quencher. Other luminescent dyes can be used to send other chemicals in a similar fashion.

The augmented microscope 100 can also be used to guide placement, movement, activation of an implantable device based upon luminescent markers. Data from position transmitters installed in the facilities can be captured and processed to present 3D stereotactic coordinates superimposed with anatomical images of the tissues. Prerecorded three-dimensional data can be obtained by MRI, CT, PET, and/or any combination thereof and provided as synthetic objects in the augmented images. The stereotactic coordinates can be used to superimpose the MRI, CT, PET, and/or any combination thereof with the real (anatomical) images with proper spatial co-registration. In some implementations, co-registered real-time imaging data can be superimposed with the real images. For example, a synthetic images including real-time intraoperative MRI of a brain tumor can be superimposed with the real (anatomical) images. The synthetic images can also include fluorescence information and/or a NIR laser beam.

The augmented microscope 100 with a NIR sensitive camera can be used to position and/or guide a laser beam within the operating field of view, such as for tissue ablation, drug delivery, or other treatment. A drug can be delivered in NIR responsive capsules and released on demand with temporal and spatial control to improve efficacy, reduce off-target toxicity. In some implementations, laser guidance can be provided using data from the position transmitters. The augmented microscope 100 can include a thermal image camera that may be used to generate a temperature map to monitor temperature distribution (e.g., during the ablation surgery). Thermal monitoring can also be obtained by projecting within the augmented microscope intraoperative MRI images obtained with any of the MRI techniques displaying temperature sensitivity (e.g., proton resonance frequency shift). The thermal information can be processed in real time to produce a temperature map or a single point read-out that can overlay the real images as illustrated in FIG. 13.

The augmented microscope 100 may also display numerical data or graphs from a patient monitoring system. For example, a real-time view of the patient's vital signs or any clinically relevant information from the hospital's intranet and applications can be displayed in the field of view. Numerical data or functions from an implantable device can also be displayed. For instance, clinical information can be extracted from an implantable device in the field of view by spectral filters.

Figure 14A:
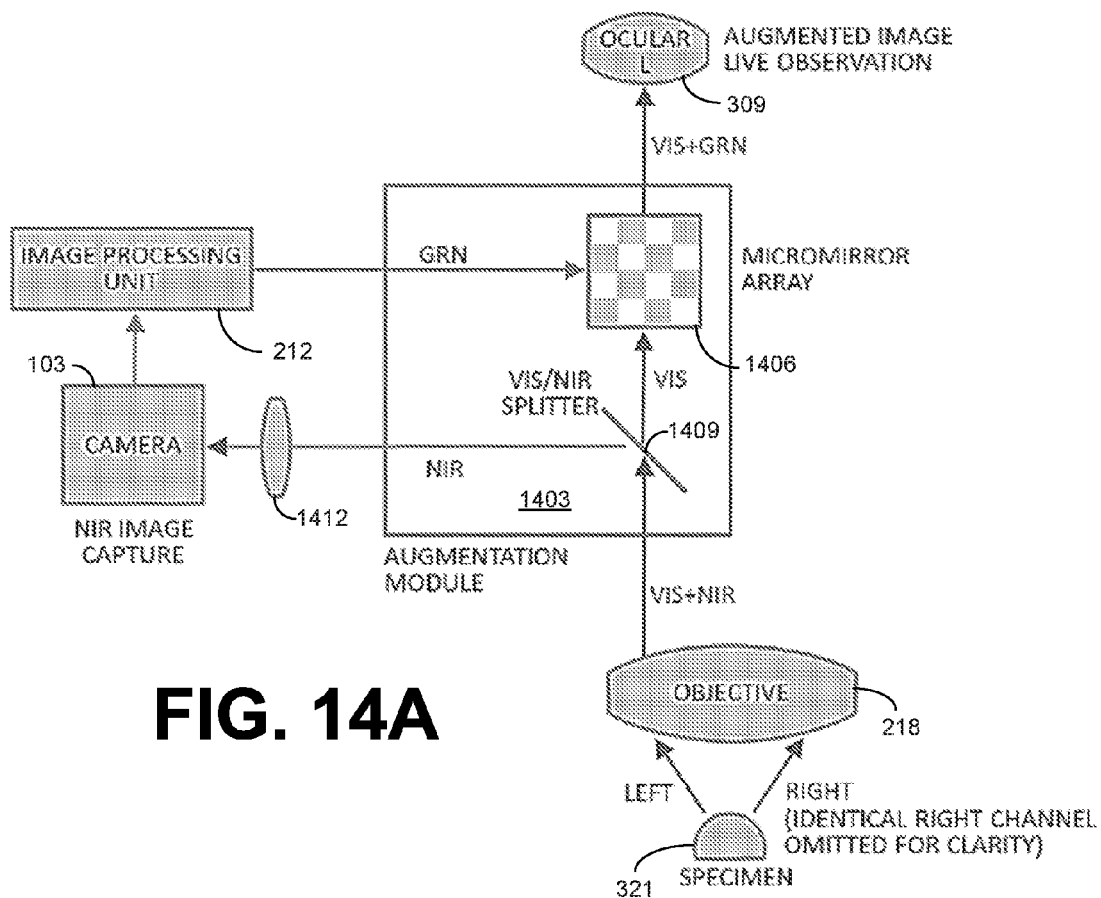
FIG. 14A is a schematic representation of an example of the augmented microscope of FIGS. 1A and 1B in accordance with various embodiments of the present disclosure.

Referring next to FIGS. 14A through 14E, shown is another example of an augmentation module configuration of the augmented stereoscopic microscope 100. As previously illustrated in FIGS. 3, 4A and 4C, the augmented microscope 100 generates an overlay of real and synthetic images in the ocular path of the microscope. For example, a real image (e.g., a color image of the surgical field) is overlaid with a synthetic image (e.g., an electronically processed NIR image of fluorescent contrast agent or pre-recorded MRI data) by projecting the synthetic image onto a beamsplitter through which the real image is transmitted. In the example of FIG. 14A, the overlay of real and synthetic images is achieved in an augmentation module 1403 using a micromirror array 1406. The micromirror array 1406 is a type of spatial light modulator (SLM) based on a micro-electro-mechanical system (MEMS). The overlay may also be accomplished using other types of SLM such as, e.g., liquid-crystal-on-silicon (LCoS), Liquid Crystal Display (LCD), switchable mirrors, or others. Some of these devices reflect light, as illustrated in the example shown in FIG. 14A, while others control light passing through them. As illustrated in FIG. 14A, the micromirror array 1406 is used to switch the image source between the optical (VIS) image and synthetic (GRN) image to produce the composite (VIS+GRN) image. The micromirror array 1406 can be fast enough to produce a flicker-less ("video frame-rate") composite of the two source images (VIS+GRN) in the ocular 309. This composite image constitutes the desired augmented image. In addition, the micromirror array 1406 can be set to deliver only the real image or only the synthetic image. The micromirror array 1406 can allow the optical throughput of the microscope to be increased and enable a full, user-controlled, transition between the real and synthetic images.

In FIG. 14A, only the left channel is illustrated for clarity, but the same configuration can be used for the right channel. A sample or specimen 321 can be illuminated with excitation light (780 nm) for excitation of ICG fluorescence (or other appropriate fluorescence agent) using an objective-mounted ring illuminator or one or more LEDs 106 that direct the excitation light though the augmentation module 1403. FIG. 4C illustrates an example of an arrangement that allows excitation light provided by the LED 106 to illuminate the sample or specimen 321 through the objective 218 of the augmented microscope 100.

Near infrared (NIR) fluorescence and visible (VIS) images can be acquired through a beamsplitter 1409 in the augmentation module 1403. The visible (VIS) image can be separated using, e.g., a dichroic beamsplitter 1409 (VIS/NIR) and directed toward the micromirror array 1406. The NIR fluorescence emission can be separated using the same dichroic beamsplitter 1409 and captured using an image forming lens 1412 and, e.g., a CMOS sensor 103. In some embodiments, the VIS and NIR images can be captured using a scientific CMOS camera 415 such as previously described with respect to FIGS. 4A and 4C. Subsequently, the NIR image can be processed by the imaging processing unit 212 to obtain the desired field of view, contrast, brightness, and/or feature extraction. In the example of FIG. 14A, a synthetic image in green (GRN) is directed toward the micromirror array 1406 using, e.g., a miniature OLED or other type of projector (not shown).

Figure 14B:
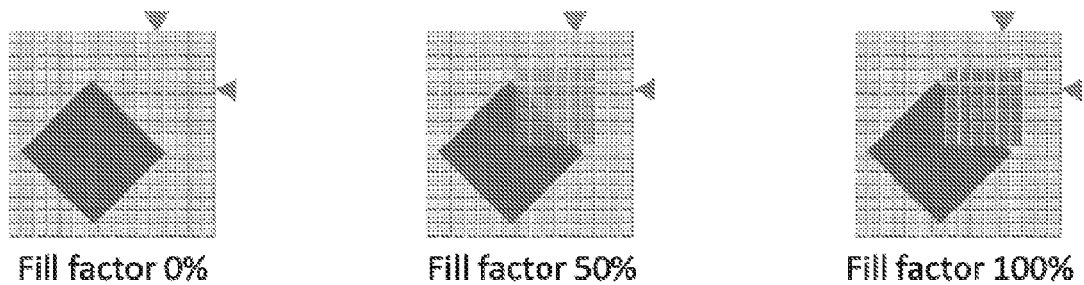

The micromirror array 1406 can be used as a switchable mirror that selects between the real image and synthetic image, and directs either one to the ocular lens 309 of the eyepiece. By switching at the frequency above the video rate, the device creates a perception of a composite image, combining the real and synthetic images. The relative contribution of the real and synthetic images is set by the duty cycle of the switchable mirror. Assuming that a mirror of the micromirror array 1406 reflects a portion of the real image when set in position 0 and the mirror reflects a portion of the synthetic image when set in position 1, the duty cycle expressed in % describes the time that the mirror spends in position 1. Thus, the duty cycle (between 0 and 100%) describes the relative contribution of the synthetic image in the composite image, which can also be referred to as the fill factor. The effect of the duty cycle is illustrated in FIG. 14B.

The operation of the mirrors in the micromirror array is further illustrated by FIGS. 14C and 14D. Each mirror in the micromirror array 1406 can be independently controlled by, e.g., the image processing unit 212. FIG. 14C is a schematic diagram depicts an example of a projection path of the real image in the augmented microscope 100. After the VIS image is separated by beamsplitter 1409 (not shown), it is directed toward the micromirror array 1406. With the mirror set in position 0, the real image can be directed to the ocular lens 309 of the eyepiece. This may be accomplished using, e.g., one or more fixed mirrors. A short-pass filter may be introduced before ocular lens 309 to block any remaining NIR light. When the mirror in the micromirror array 1406 is repositioned to position 1, the synthetic image generated by a light source is directed to the ocular lens 309 of the eyepiece as shown in FIG. 14D.

By switching the mirrors of the micromirror array 1406 between position 0 and position 1, an augmented image can be generated. In one embodiment, the synthetic image can be generated by, e.g., a LED projector with all mirrors of the micromirror array 1406 switching simultaneously. Here, the entire micromirror array 1406 acts as one switchable mirror, whereas the pixels are generated in the LED projector. In another embodiment, the synthetic image can be generated by illumination with a high power light source such as, e.g., a metal halide lamp. In this situation, each mirror of the micromirror array 1406 is individually controlled and becomes a single pixel of the synthetic image, with the intensity of each pixel controlled by the duty cycle of the switching pattern. The light source provides no pixels. The advantage of individually switching the mirrors of the micromirror array 1406 is that it allows for increased brightness of images, which can be controlled by the output of the metal halide lamp. When all the mirrors of the micromirror array 1406 are switched simultaneously, the brightness is limited to how much light one can be provided by the LED projector, which can be significantly less than that provided by a metal halide lamp.

Figure 14E:
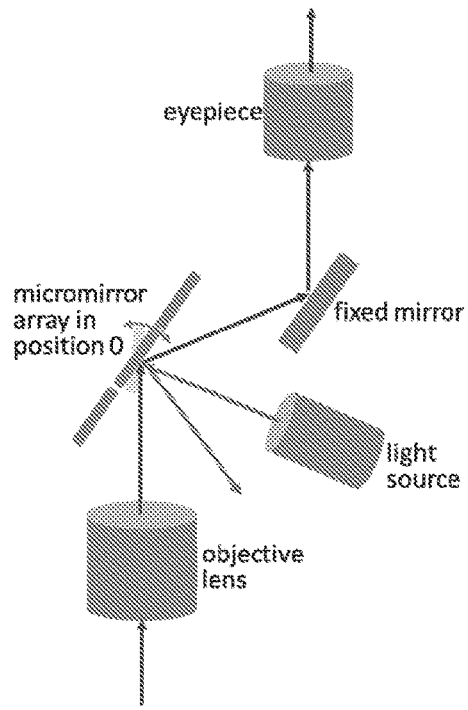
Figure 14E:
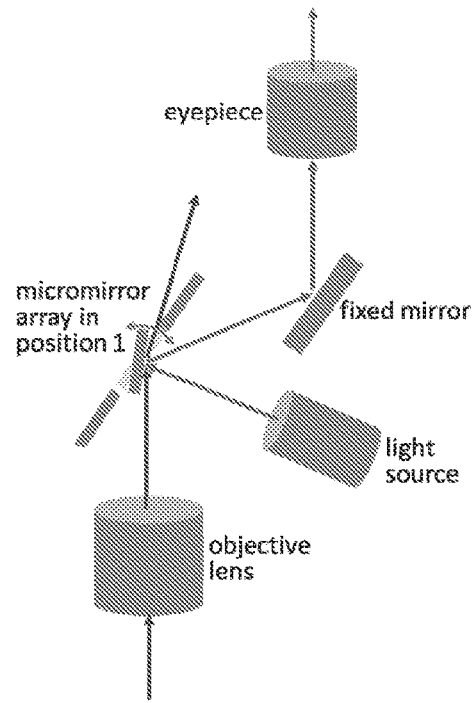
Figure 14E:
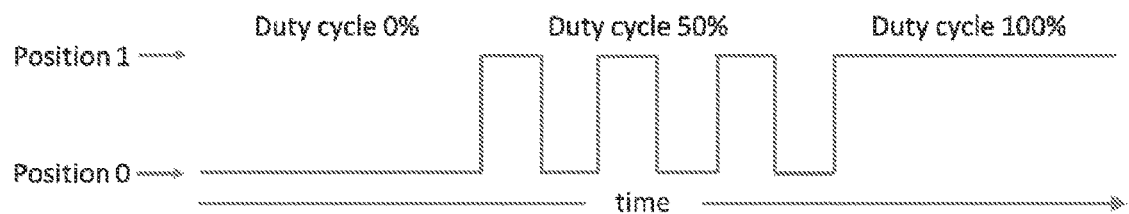

FIG. 14E shows an example of a switching sequence applied to one of the mirrors of the micromirror array 1406. The mirror can be retained in position 0 (as shown in FIG. 14C), which continuously directs the real image to the eyepiece, or it can be retained in position 1, which continuously directs the synthetic image to the eyepiece. By intermittently switching the mirror between positions 0 and 1, a combination of the real and synthetic images can be visible in the eyepiece. In the example of FIG. 14E, these possibilities are illustrated by the 0%, 100%, and 50% duty cycles. A high frequency switching, generally above 30 Hz, will produce a perception of a steady image with contribution of real and synthetic images. A varying duty cycle will produce a varying balance of the real and synthetic image in the eyepiece.

Representative examples of images seen on the micromirror array are illustrated in FIG. 14B. The diamond represents a real image reflected by the micromirror array 1406. The square represents a synthetic image introduced by directing selected mirrors to transiently reflect green light corresponding to a NIR image. Each of the micromirrors acts as a single pixel that can be independently switched between position 0 (real image) and 1 (synthetic image). In the example of FIG. 14B, the dark arrows point to a single mirror whose switching pattern can be described by the sequence shown in FIG. 14E. The fill factor is controlled by the switching pattern, 0%, 50%, or 100%, and determines the balance between the synthetic (square) and real (diamond) images.

The use of a micromirror array 1406 allows for the generation of synthetic images of very high intensity, limited only by the intensity of the auxiliary light source. This can enhance the augmented images produced using the augmentation modules of FIGS. 3 and 4A-4C, where brightness of the images may be limited by the optical power output of certain projection devices such as OLEDs. Also, when not transmitting the synthetic image (in position 0), the mirrors of the micromirror array 1406 do not reduce the optical throughput of the real image (in position 0) through the augmented microscope.

In some implementations, synthetic images other than that produced by the NIR camera (or sensor) 103 can be combined with the visible bright-field images by projecting the synthetic images onto the micromirror array 1406 to generate composite images with the visible bright-field images. For example, the image processing unit 212 can be used to provide prerecorded information obtained through MRI, CT, or PET scans of the examined object. Real-time synthetic images (e.g., chemical concentration or thermal images obtained from thermal cameras or various fluorescence detectors such as, but not limited to, fluorescence intensity decay and/or polarization in the visible, near infrared and/or ultraviolet ranges can also be acquired and combined with the visible bright-field images using the image processing unit 212.

It should be emphasized that the above-described embodiments of the present disclosure are merely possible examples of implementations set forth for a clear understanding of the principles of the disclosure. For example, the augmentation method is not limited to the micro-electro-mechanical systems (MEMS) discussed herein. This augmentation can be similarly accomplished using other types of spatial light modulators such as, e.g., liquid-crystal-on-silicon (LCoS), Liquid Crystal Display (LCD), switchable mirrors, or other controllable micromirror array. Some of these devices reflect light, as illustrated in the example shown in FIG. 14A, while others control light passing through them. Many variations and modifications may be made to the above-described embodiment(s) without departing substantially from the spirit and principles of the disclosure. All such modifications and variations are intended to be included herein within the scope of this disclosure and protected by the following claims.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" includes traditional rounding according to significant figures of numerical values. In addition, the phrase "about 'x' to 'y'" includes "about 'x' to about 'y'".

Therefore, at least the following is claimed:

1. An augmented stereoscopic microscope, comprising:
   an objective lens configured to simultaneously receive near infrared (NIR) images and visible bright-field images of an examined object; and
   an augmentation module positioned between the objective lens and an eyepiece of the augmented stereoscopic microscope, the augmentation module configured to:
      separate at least a portion of the NIR images from the visible bright-field images received from the objective lens thereby producing separated NIR images that are independently directed for capture by a sensor and processing by an image processing unit to produce synthetic images based upon the separated NIR images; and
      combine the synthetic images projected in the augmented module with the visible bright-field images received from the objective lens to form co-registered augmented images that are directed to and visible through the eyepiece of the augmented stereoscopic microscope.

2. The augmented stereoscopic microscope of claim 1, wherein the augmentation module comprises a beamsplitter configured to combine the synthetic images projected in the augmented module with the visible bright-field images to form the co-registered augmented images.

3. The augmented stereoscopic microscope of claim 2, wherein the synthetic images are projected onto the beamsplitter to overlay the visible bright-field images projecting through the beamsplitter.

4. The augmented stereoscopic microscope of claim 2, wherein the beamsplitter is a dichroic beamsplitter.

5. The augmented stereoscopic microscope of claim 1, wherein the augmentation module comprises a spatial light modulator configured to combine the synthetic images projected in the augmented module with the visible bright-field images to form the co-registered augmented images.

6. The augmented stereoscopic microscope of claim 5, wherein the spatial light modulator is a micromirror array or a switchable mirror.

7. The augmented stereoscopic microscope of claim 6, wherein combining the synthetic images projected in the augmented module with the visible bright-field images comprises switching at least a portion of the micromirror array to alternate between reflecting at least a portion of the synthetic images and at least a portion of the visible bright-field images.

8. The augmented stereoscopic microscope of claim 1, wherein the synthetic images comprise visible pseudo-color images.

9. The augmented stereoscopic microscope of claim 1, wherein the augmentation module comprises a light emitting diode (LED) configured to illuminate the examined object with NIR excitation light via the objective lens.

10. The augmented stereoscopic microscope of claim 1, wherein the augmentation module comprises the sensor, which is configured to capture the separated NIR images.

11. The augmented stereoscopic microscope of claim 10, wherein the sensor is further configured to capture the co-registered augmented images.

12. The augmented stereoscopic microscope of claim 1, wherein the augmentation module comprises another sensor configured to capture the co-registered augmented images.

13. The augmented stereoscopic microscope of claim 1, wherein the augmentation module comprises a short-pass filter configured to remove NIR light from the co-registered augmented images directed to the eyepiece.

14. The augmented stereoscopic microscope of claim 1, wherein the augmentation module is configured to form co-registered augmented images for a right optical path of the augmented stereoscopic microscope and co-registered augmented images for a left optical path of the augmented stereoscopic microscope.

15. The augmented stereoscopic microscope of claim 1, wherein the synthetic images comprise prerecorded information associated with the examined object.

16. The augmented stereoscopic microscope of claim 15, wherein the prerecorded information is obtained through magnetic resonance imaging (MRI), computed tomography (CT), or positron emission tomography (PET) of the examined object.

17. A method, comprising:
obtaining a near infrared (NIR) image of an examined object separated from an optical path between an objective lens and an eyepiece of an augmented stereoscopic microscope, the NIR image obtained independent of visual images;
generating a synthetic image based upon the NIR image;
combining the synthetic image with a real-time visual image of the examined object by projecting the synthetic image to form an augmented image in the optical path; and
directing the augmented image along the optical path to the eyepiece of the augmented stereoscopic microscope.

18. The method of claim 17, wherein combining the synthetic image with the real-time visual image comprises projecting the synthetic image onto a beamsplitter to overlay the real-time visual image.

19. The method of any of claim 17, wherein combining the synthetic image with the real-time visual image comprises switching at least a portion of a micromirror array to reflect at least a portion of the synthetic image and at least a portion of the real-time visual image.

20. The method of claim 17, comprising illuminating the examined object with NIR excitation through the objective lens of the augmented stereoscopic microscope.

21. The method of claim 17, wherein a NIR laser beam directed toward the examined object is visible in the synthetic image and the augmented image.

22. The method of claim 17, wherein the synthetic image comprises an indication of a chemical concentration in the examined object.

23. The method of claim 17, wherein the synthetic image comprises an indication of a temperature of the examined object.

* * * * *